(12) United States Patent
Yukimune et al.

(10) Patent No.: US 6,403,343 B2
(45) Date of Patent: *Jun. 11, 2002

(54) METHOD OF PRODUCING A TAXANE-TYPE DITERPENE AND A METHOD OF OBTAINING CULTURED CELLS WHICH PRODUCE THE TAXANE-TYPE DILTERPENE AT A HIGH RATE

(75) Inventors: Yukihito Yukimune; Yasuhiro Hara; Yosuke Higashi; Naoto Ohnishi; Homare Tabata; Chuzo Suga; Kouichi Matsubara, all of Yamaguchi (JP)

(73) Assignee: Mitsui Chemicals, Inc., Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/301,075

(22) Filed: Apr. 28, 1999

Related U.S. Application Data

(62) Division of application No. 08/808,218, filed on Feb. 28, 1997, now Pat. No. 5,968,789, which is a division of application No. 08/491,844, filed on Jul. 14, 1995, now Pat. No. 5,637,484.

(30) Foreign Application Priority Data

| Nov. 15, 1993 | (JP) | 5-284893 |
| Mar. 7, 1994 | (JP) | 6-36156 |
| May 18, 1994 | (JP) | 6-104211 |
| May 18, 1994 | (JP) | 6-104212 |
| May 18, 1994 | (JP) | 6-104213 |
| Jun. 28, 1994 | (JP) | 6-146826 |
| Aug. 25, 1994 | (JP) | 6-201150 |
| Aug. 25, 1994 | (JP) | 6-201151 |
| Oct. 18, 1994 | (JP) | 6-252528 |

(51) Int. Cl.$^7$ ............................................ C12P 17/02
(52) U.S. Cl. .................. 435/123; 435/244; 435/420; 435/431; 549/510; 549/511
(58) Field of Search ................ 435/123, 244, 435/420, 431; 549/510, 511

(56) References Cited

U.S. PATENT DOCUMENTS 5,015,744 A 5/1991 Holton
5,019,504 A 5/1991 Christen et al.
5,407,816 A 4/1995 Bringi et al.

FOREIGN PATENT DOCUMENTS

| EP | 41 22 208 C1 | 7/1992 |
| EP | 0 521 435 A2 | 1/1993 |
| WO | WO 93/17121 | 9/1993 |

OTHER PUBLICATIONS

E.R.M. Wickremesine et al., 1992 World Congress on Cell and Tissue Culture, Develpoment of callus and cell suspension . . . , vol. 28, No. 3, Mar., 1992.

Hackh's Chemical Dictionary, Fifth Ed. 1987, p. 56.

*Primary Examiner*—Irene Marx
(74) *Attorney, Agent, or Firm*—Birch, Stewart, Kolasch & Birch, LLP

(57) ABSTRACT

This invention relates to a method of producing a taxane-type diterpene(s) wherein tissues or cells of a plant which produces taxane-type diterpene(s) is cultured in the presence of at least one selected from the group consisting of jasmonic acids, compounds containing a heavy metal, complex ions containing a heavy metal, heavy metal ions, amines and antiethylene agents, a method of producing a taxane-type diterpene wherein the tissues or the cells of the plant are cultured by controlling the oxygen concentration in a gas phase in a culture vessel to less than the oxygen concentration in the atmosphere from the initial stage of the culture, or by controlling the dissolved oxygen concentration in a fluid medium which is in contact with the tissue or the cell to less than the saturated dissolved oxygen concentration at that temperature from the initial stage of the culture, a method of producing a taxane-type diterpene wherein the tissue or the cell of the plant is cultured in a culture vessel, while oxygenic gas containing 0.03–10 % of carbon dioxide is used as aeration gas to be introduced to the vessel, and a method of obtaining highly productive cultured cells for the taxane-type diterpene wherein cultured cells of the plant which produces the taxane-type diterpene are separated into a plurality of layers according to the difference in their specific gravities, and the cells contained in at least one layer are cultured, then highly productive cultured cells for the taxane-type diterpene are selected from among those cultured cells.

The present invention allows industrial production of a taxane-type diterpene such as taxol which is useful as a therapeutic agent for cancer.

15 Claims, 7 Drawing Sheets

METHOD OF PRODUCING A TAXANE-TYPE DITERPENE AND A METHOD OF OBTAINING CULTURED CELLS WHICH PRODUCE THE TAXANE-TYPE DILTERPENE AT A HIGH RATE

This application is a divisional of application Ser. No. 08/808,218, filed on Feb. 28, 1997 now U.S. Pat. No. 5,968,789, which is a divisional application of application Ser. No. 08/491,844 filed Jul. 14, 1995 (U.S. Pat. No. 5,637,484) the entire contents of which are hereby incorporated by reference.

TECHNICAL FIELD

This invention relates to a method of producing a taxane-type diterpene including taxol which is useful as a therapeutic agent for ovarian cancer, mammary cancer, lung cancer and the like, and a method of obtaining cultured cells which produce the taxane-type diterpene at a high rate.

BACKGROUND ART

Taxol, which is useful as a therapeutic agent for ovarian cancer, mammary cancer, lung cancer and the like, is a taxane-type diterpene identified after being isolated from *Taxus brevifolia* NUTT, which is a plant belonging to genus Taxus, family Taxaceae and has a complex ester group which is related to its activity. Taxol can be found in all the parts of the plant body of *Taxus brevifolia* NUTT, but the bark has been reported to exceed all others in its content of the taxol. At present, taxol is collected from a natural or a cultivated plant body, however, the plant belonging to genus Taxus grows slowly, and it takes more than 10 years to grow to a height of 20 cm above the ground. Also the tree dies after its bark is taken off, thus it has been difficult to easily obtain a large amount of taxol. It would be advantageous if a taxane-type diterpene such as taxol and baccatin III which is a precursor of taxol, can be produced by the use of tissue culture, since a large amount of taxol can be easily obtained without cutting down the trees.

As a conventional method of producing taxol by utilizing cultured plant cells, a US patent was issued on a production method utilizing cultured cells of *Taxus brevifolia* NUTT (U.S. Pat. No. 5,019,504), however, the yield of taxol production described therein is 1–3 mg/l, and that is insufficient for the industrial production. Also, the production of taxol by the cell culture is unstable and even when a primary cell of high productivity can be obtained by selection, it is difficult to keep its content by subculturing [E. R. M. Wickremesine et al., World Congress on Cell and Tissue Culture (1992)].

On the other hand, as a prior art in the taxol production, a semisynthetic method from baccatin III, which is a precursor in biosynthesis of taxol, is disclosed in the specification of U.S. Pat. No. 5,015,744 issued to Holton et al. By the use of the plant tissue culture, a raw material for the semisynthetic process such -as baccatin III can be produced, thus the plant tissue culture can be also utilized for taxol production by the above-mentioned semisynthetic process.

DISCLOSURE OF INVENTION

The first object of the present invention is to provide a simple method of producing a taxane-type diterpene by plant tissue culture.

The second object of the present invention is to provide a method of obtaining cultured cells which produce a taxane-type diterpene at a high rate.

The first invention of the present application is a method of producing a taxane-type diterpene wherein a tissue or a cell of a plant which produces a taxane-type diterpene is cultured in the presence of at least one substance selected from the group consisting of jasmonic acids, compounds containing a heavy metal, complex ions containing a heavy metal, heavy metal ions, amines and antiethylene agents, then the taxane-type diterpene is recovered from the resulting cultures.

The second invention of the present application is a method of producing a taxane-type diterpene wherein a tissue or a cell of a plant which produces a taxane-type diterpene is cultured by controlling the oxygen concentration in a gas phase in a culture vessel to less than the oxygen concentration in the atmosphere, from the initial stage of the culture, or by controlling the dissolved oxygen concentration in a fluid medium which is in contact with the tissue or the cell to less than the saturated dissolved oxygen concentration at that temperature, from the initial stage of the culture, then the taxane-type diterpene is recovered from the resulting cultures.

The third invention of the present application is a method of obtaining cultured cells which produce a taxane-type diterpene at a high rate, wherein cells of a plant which produces a taxane-type diterpene are fractionated into a plurality of layers according to the difference in their specific gravities, and cells contained in at least one layer are cultured, then such cultured cells that produce the taxane-type diterpene at a high rate are selected from among those cultured cells.

The present invention will be described in further detail.

The taxane-type diterpene, which is an object for the present invention, is not particularly limited to any diterpene as far as it has a taxane skeleton, and the illustrative examples include taxol, 7-epitaxol, baccatin III, 7-epibaccatin III, cephalomannine, 7-epicephalomannine, 10-deacetylbaccatin III, 10-deacetylcephalomannine, 10-deacetyltaxol, taxagifine, an analogue thereof, taxane 1a, an analogue thereof, xylosyl cephalomannine, xylosyl taxol and the like.

Examples of the plant to be used in the present invention which produces the taxane-type diterpene are those belonging to genus Taxus, such as Taxus baccata LINN, Taxus cuspidata SIEB. et ZUCC, Taxus cuspidata SIEB. et ZUCC var. nana REHDER, Taxus brevifolia NUTT, Taxus canadiensis MARSH, Taxus chinensis, and Taxus media.

According to the first invention of the present application, culture of the above-mentioned plant can be carried out by the previously known method except that the tissue or the cell of the plant which produces the taxane-type diterpene is cultured in the presence of at least one substance selected from the group consisting of jasmonic acids, compounds containing a heavy metal, complex ions containing a heavy metal, heavy metal ions, amines and antiethylene agents.

Examples of jasmonic acids, which are objects for the first invention of the present application, include a compound represented by the general formula (I):

(I)

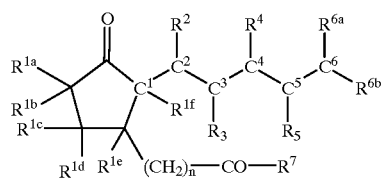

[wherein, $R^{1a}$, $R^{1b}$, $R^1c$, $R^{1d}$, $R^{1e}$ and $R^{1f}$ respectively represent hydrogen atom, hydroxyl group, alkyl group having 1 to 6 carbon atoms, or alkoxy group having 1 to 6 carbon atoms;

$R^2$, $R^3$, $R^4$, $R^5$ and $R^{6a}$ respectively represent hydrogen atom or alkyl group having 1 to 6 carbon atoms;

a side chain consisting of $C^1$—$C^2$—$C^3$—$C^4$—$C^5$—$C^6$ may contain one or more double bonds;

$R^{6b}$ represents hydroxyl group or —O—carbohydrate residue;

$R^7$ represents hydroxyl group, OM (wherein M is alkali metal atom, alkaline earth metal atom or $NH_4$), $NHR^8$ (wherein $R^8$ represents hydrogen atom, acyl group having 1 to 6 carbon atoms, alkyl group having 1 to 6 carbon atoms or amino acid residue), $OR^9$ (wherein $R^9$ is alkyl group having 1 to 6 carbon atoms or carbohydrate residue), or alkyl group having 1 to 6 carbon atoms;

n is an integer of 1–7;

and in the above-mentioned five-membered ring, a double bond may be formed between the neighboring member carbon atoms], a compound represented by the general formula (II):

(II)

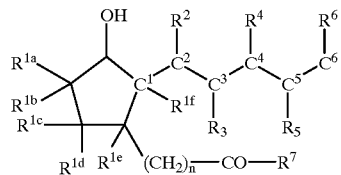

[wherein, $R^{1a}$, $R^{1b}$, $R^{1c}$, $R^{1d}$, $R^{1e}$ and $R^{1f}$ respectively represent hydrogen atom, hydroxyl group, alkyl group having 1 to 6 carbon atoms, or alkoxy group having 1 to 6 carbon atoms;

$R^2$, $R^3$, $R^4$, $R^5$ and $R^6$ respectively represent hydrogen atom or alkyl group having 1 to 6 carbon atoms;

a side chain consisting of $C^1$—$C^2$—$C^3$—$C^4$—$C^5$—$C^6$ may contain one or more double bonds;

$R^7$ represents hydroxyl group, OM (wherein M is alkali metal atom, alkaline earth metal atom or $NH_4$), $NHR^8$ (wherein $R^8$ represents hydrogen atom, acyl group having 1 to 6 carbon atoms, alkyl group having 1 to 6 carbon atoms or amino acid residue), $OR^9$ (wherein $R^9$ is alkyl group having 1 to 6 carbon atoms or carbohydrate residue), or alkyl group having 1 to 6 carbon atoms;

n is an integer of 1–7;

and in the above-mentioned five-membered ring, a double bond may be formed between the neighboring member carbon atoms], and a compound represented by the general formula (III):

(III)

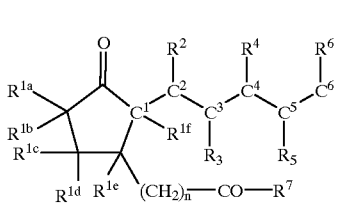

[wherein, $R^{1a}$, $R^{1b}$, $R^{1c}$, $R^{1d}$, $R^{1e}$ and $R^{1f}$ respectively represent hydrogen atom, hydroxyl group, alkyl group having 1 to 6 carbon atoms, or alkoxy group having 1 to 6 carbon atoms;

$R^2$, $R^3$, $R^4$, $R^5$ and $R^6$ respectively represent hydrogen atom or alkyl group having 1 to 6 carbon atoms;

a side chain consisting of $C^1$—$C^2$—$C^3$—$C^4$—$C^5$—$C^6$ may contain one or more double bonds;

$R^7$ represents hydroxyl group, OM (wherein M is alkali metal atom, alkaline earth metal atom or $NH_4$), $NHR^8$ (wherein $R^8$ represents hydrogen atom, acyl group having 1 to 6 carbon atoms, alkyl group having 1 to 6 carbon atoms or amino acid residue), $OR^9$ (wherein $R^9$ is alkyl group having 1 to 6 carbon atoms or carbohydrate residue), or alkyl group having 1 to 6 carbon atoms;

n is an integer of 1–7;

and in the above-mentioned five-membered ring, a double bond may be formed between the neighboring member carbon atoms].

Preferable examples of jasmonic acids represented by the above-mentioned general formula (I) include a compound represented by the general formula (I'):

(I')

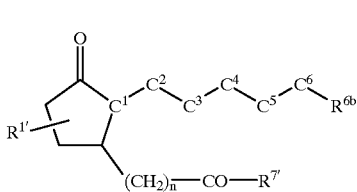

[wherein, $R^1$ represents hydrogen atom or hydroxyl group;

a side chain consisting of $C^1$—$C^2$—$C^3$—$C^4$—$C^5$—$C^6$ may contain a double bond between $C^1$ and $C^2$, between $C^2$ and $C^3$, or between $C^3$ and $C^4$;

$R^{6b}$ represents hydroxyl group or —O—carbohydrate residue;

$R^{7'}$ represents hydroxyl group, OM (wherein M is alkali metal atom, alkaline earth metal atom or $NH_4$), $NHR^8$ (wherein $R^{8'}$ represents hydrogen atom, acyl group having 1 to 4 carbon atoms, alkyl group having 1 to 4 carbon atoms or amino acid residue) or $OR^{9'}$ (wherein $R^{9'}$ represents alkyl group having 1 to 4 carbon atoms or carbohydrate residue);

n is an integer of 1–7;

and in the above-mentioned five-membered ring, a double bond may be formed between the neighboring member carbon atoms], and preferable examples of jasmonic acids represented by the above-mentioned general formula (II) include a compound represented by the general formula (II'):

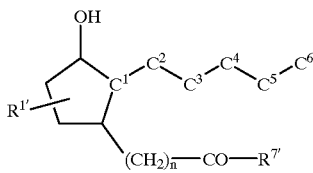

(II')

[wherein, $R^{1'}$ represents hydrogen atom or hydroxyl group;
a side chain consisting of $C^1$—$C^2$—$C^3$—$C^4$—$C^5$—$C^6$ may contain a double bond between $C^1$ and $C^2$, between $C^2$ and $C^3$, or between $C^3$ and $C^4$;
$R^{7'}$ represents hydroxyl group, OM (wherein M is alkali metal atom, alkaline earth metal atom or $NH_4$), $NHR^{8'}$ (wherein $R^{8'}$ represents hydrogen atom, acyl group having 1 to 4 carbon atoms, alkyl group having 1 to 4 carbon atoms or amino acid residue) or $OR^{9'}$ (wherein $R^{9'}$ represents alkyl group having 1 to 4 carbon atoms or carbohydrate residue);
n is an integer of 1–7;
and in the above-mentioned five-membered ring, a double bond may be formed between the neighboring member carbon atoms], and preferable examples of jasmonic acids represented by the above-mentioned general formula (III) include a compound represented by the general formula (III'),

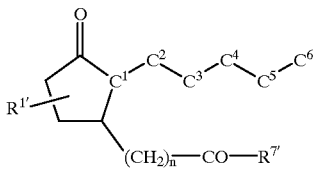

(III')

[wherein, $R^{1'}$ represents hydrogen atom or hydroxyl group;
a side chain consisting of $C^1$—$C^2$—$C^3$—$C^4$—$C^5$—$C^6$ may contain a double bond between $C^1$ and $C^2$, between $C^2$ and $C^3$, or between $C^3$ and $C^4$;
$R^{7'}$ represents hydroxyl group, OM (wherein M is alkali metal atom, alkaline earth metal atom or $NH_4$), $NHR^{8'}$ (wherein $R^{8'}$ represents hydrogen atom, acyl group having 1 to 4 carbon atoms, alkyl group having 1 to 4 carbon atoms or amino acid residue) or $OR^{9'}$ (wherein $R^{9'}$ represents alkyl group having 1 to 4 carbon atoms or carbdhydrate residue);
n is an integer of 1–7;
and in the above-mentioned five-membered ring, a double bond may be formed between the neighboring member carbon atoms].

In the above-mentioned general formulae (I), (II) and (III), examples of alkyl group having 1 to 6 carbon atoms represented by $R^{1a}$, $R^{1b}$, $R^{1c}$, $R^{1d}$, $R^{1e}$, $R^{1f}$, $R^2$, $R^3$, $R^4$, $R^5$, $R^6$, $R^{6a}$, $R^7$, $R^8$ or $R^9$ include, for example, methyl, ethyl, n-propyl, isopropyl, n-butyl, isobutyl, sec-butyl, t-butyl, n-pentyl, and n-hexyl groups.

In the above-mentioned general formulae (I), (II) and (III), examples of alkoxy group having 1 to 6 carbon atoms represented by $R^{1a}$, $R^{1b}$, $R^{1c}$, $R^{1d}$, $R^{1e}$ or $R^{1f}$ include, for example, methoxy, ethoxy, n-propoxy, isopropoxy, n-butoxy, isobutoxy, sec-butoxy, t-butoxy, n-pentyloxy and n-hexyloxy groups.

When $R^7$ is OM, examples of an alkali metal atom or an alkaline earth metal atom represented by M include, for example, sodium, potassium and calcium.

When $R^7$ is $NHR^8$, the acyl group having 1 to 6 carbon atoms represented by $R^8$ may have either a straight chain or a branched chain, and their examples include, for example, formyl, acetyl, propionyl, butyryl, valeryl, hexanoyl and acryloyl groups.

When $R^7$ is $NHR^8$, examples of an amino acid residue represented by $R^8$ include isoleucyl, tyrosyl, and tryptophyl groups.

When $R^7$ is $OR^9$, an example of a carbohydrate residue represented by $R^9$ is glucopyranosyl group, and when $R^{6b}$ is —O—carbohydrate residue in the above-mentioned general formula (I), an example of a carbohydrate residue is glucopyranosyl group.

In the compounds represented by the general formulae (I), (II) and (III), a double bond may be formed between the neighboring member carbon atoms in the five-membered ring.

Illustrative examples of the compound represented by the general formula (I) include those shown as follows;

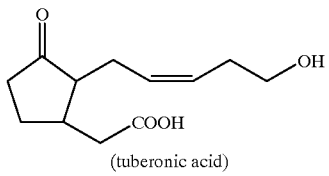

(Compound A)

(tuberonic acid)

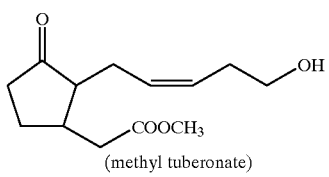

(Compound B)

(methyl tuberonate)

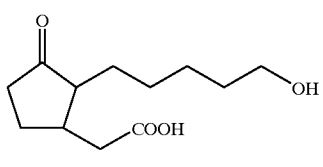

(Compound C)

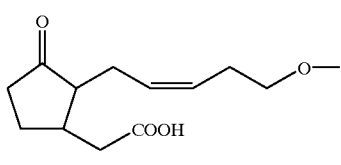

(Compound D)

Illustrative examples of the compound represented by the general formula (II) include those shown as follows;

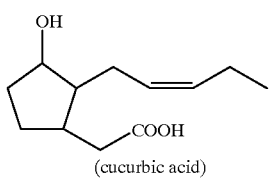

(Compound E)

(cucurbic acid)

-continued (Compound F)

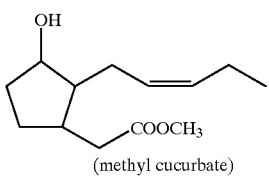
(methyl cucurbate)

(Compound G)

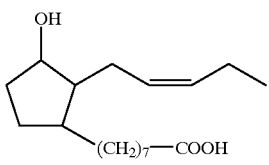

(Compound H)

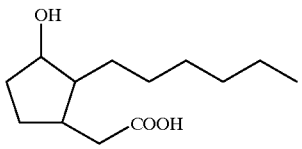

Illustrative examples of the compound represented by the general formula (III) include those shown as follows;

(Compound I)

$R^{1a}, R^{1b}, R^{1c}, R^{1d}, R^{1e}, R^{1f}, R^2, R^3, R^4, R^5, R^6$: H

A double bond is formed between $C^3$ and $C^4$.

$R^7$: —OH or —OCH$_3$ n: 1 to 3

(Compound J)

$R^{1a}, R^{1b}, R^{1c}, R^{1d}, R^{1e}, R^{1f}, R^2, R^3, R^4, R^5, R^6$: H $R^7$: —OH n: 1

Illustrative examples of the compound represented by the general formula (III) wherein $R^{1a}, R^{1b}, R^{1c}, R^{1d}, R^{1e}$ or $R^{1f}$ is hydroxyl group, or a double bond is formed between the neighboring member carbon atoms in the five-membered ring, include those shown as below;

(Compound K)

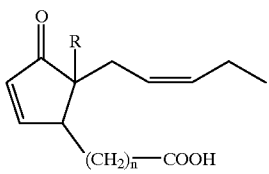
(1) n = 1, R = H
(2) n = 7, R = H
(3) n = 7, R = OH (Compound L)

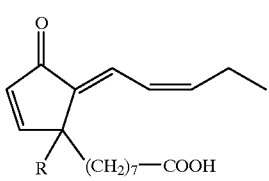
(1) R = H
(2) R = OH

-continued (Compound M)

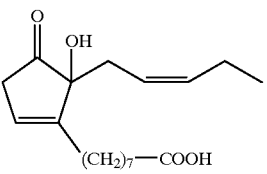

(Compound N)

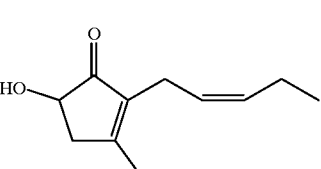

Preferable examples of a compound represented by the general formula (I), (II) or (III) include the compounds wherein $R^{1a}, R^{1b}, R^{1c}, R^{1d}, R^{1e}, R^{1f}, R^2, R^3, R^4, R^5$ and $R^6$ are hydrogen atoms, $R^7$ is hydroxyl group or methoxy group, and a side chain consisting of $C^1$—$C^2$—$C^3$—$C^4$—$C^5$—$C^6$ does not contain a double bond, or contain a double bond between $C^1$ and $C^2$, between $C^2$ and $C^3$, or between $C^3$ and C4.

Jasmonic acids to be used in the present invention which are represented by the general formula (I), (II) or (III) have various stereoisomers (cis-trans isomers and optical isomers), and each isomer can be used alone or in the form of a mixture.

All of the jasmonic acids shown above have the effect of improving the productivity in the taxane-type diterpene production, however, tuberonic acid, methyl tuberonate, cucurbic acid, methyl cucurbate, jasmonic acid and methyl jasmonate, which are the compounds represented by the general formula (I), (II) or (III) wherein $R^{1a}, R^{1b}, R^{1c}, R^{1d}, R^{1e}, R^{1f}, R^2, R^3, R^4, R^5$ and $R^6$ are hydrogen atoms, $R^7$ is hydroxyl group or methoxy group, n is 1, and a double bond is formed between $C^3$ and $C^4$, are particularly preferable from the view point of their high effectiveness in improving the productivity.

These jasmonic acids are prepared by synthesis or extraction and the like from a plant (H. Yamane et al: Agric. Biol. Chem., 44, 2857–2864(1980)).

By the way, there is a description teaching that jasmonic acids are produced by various plants by themselves as a phytohormone-like substance which induces various reactions related to growth promotion, maturation of tissue and appearance of resistance to disease (Teruhiko Yoshihara. Shokubutsu Saibō Kōgaku, Vol 2, No.4 523–531 (1990)).

Accordingly, the jasmonic acids involved in the present invention, can be not only added from outside of the culture system, but also produced by the cultured cells or cultured tissues by themselves. An example of a method to promote the production of such endogenous jasmonic acids by the cultured cells or cultured tissues includes addition of microorganism cultures, an extract or a heat-treated substance thereof, or a plant extract to a culture medium, and an illustrative example of such a method is a process of adding a fungus cell wall fraction described by M. J. Mueller et al., Proc. Natl. Acad. Sci. U.S.A., 90 (16), 7490–7494 (1993)). It is also possible to increase the amount of the produced endogenous jasmonic acid by partially damaging cultured cells or cultured tissues mechanically, or with ultraviolet rays, or heat, and one illustrative example of such a process is mechanical cytoclasis of a part of cells (R. A. Cleeman et al., Proc. Natl. Acad. Sci. U.S.A., 89(11), 4938–4941 (1989).

Since jasmonic acids are hardly soluble in water, they are usually dissolved in an organic solvent such as ethanol and methanol or dissolved in a surfactant and the like, then added to a culture medium. Jasmonic acids in liberated form can be used as they are, or they are used in the form of a salt by being neutralized with an alkali.

Of the jasmonic acids, those compounds represented by the formula (I) or (III) tend to be in stable trans-form rather than unstable cis-form, since epimerization occurs at the alpha-position to the carbonyl group in the five-membered ring by an acid, an alkali or heat. In an equilibrium experiment utilizing natural or synthesized jasmonic acids, the trans-form is present in the ratio of 90% and the cis-form is present in the ratio of 10%. Generally, cis-form is considered to have a higher activity, but jasmonic acids to be used in the present invention include all the stereoisomers of the compounds represented by the above-mentioned formula (I) or (III), and the mixture thereof.

Jasmonic acids are required to have a concentration in a culture medium of 0.01–1000 $\mu$M, and it is particularly preferable, according to the first invention of the present application, to control the concentration of the jasmonic acids to be in the range of 0.1 to 500 $\mu$M.

Induction of some secondary metabolites by addition of jasmonic acids to plant cell cultures is described in DE 4122208 C1, however, there have been no reports on carrying out tissue culture of a taxane-type diterpene producing plant in the presence of jasmonic acids as a medium additive, and it has been beyond all expectations that the amount of the produced taxane-type diterpene, which has totally different biosynthetic pathway or biosynthesis controlling mechanism from those of the secondary metabolites disclosed in the above-mentioned patent, was increased by the method of the first invention of the present application.

There is a description in the International Publication WO No. 93/17121 that jasmone or methyl jasmone, which has a structure analogous to those of jasmonic acids represented by the formula (I), (II) or (III) to be used in the present invention, is effective in induction of taxol production. However, these compounds do not have a group such as carboxyl, which is represented by the formula: $-(CH_2)_n-CO-R^7$ in the formula (I), (II) or (III), unlike the jasmonic acids, and the taxol inducing activity of these compounds was found to be low (see Comparative Example No. 24).

The heavy metals, which are objects for the first invention of the present application, are not particularly limited to any heavy metal as far as it belongs to the copper group or the iron group, however, as the metal belonging to the copper group, the use of silver is particularly preferable, and as the metal belonging to the iron group, the use of cobalt is particularly preferable. In addition to that, when silver or cobalt is used, it is preferably used in the form of a compound containing the said heavy metal, a complexion containing the said metal or in the form of the said metal ion. These compounds can be used alone or in combination.

Illustrative examples of the compound containing silver include silver nitrate, silver sulfate, silver fluoride, silver chlorate, silver perchlorate, silver acetate, silver sulfite, silver hexafluorophosphate(V), silver tetrafluoroborate, diamine silver(I) sulfate, potassium diaminoargentate(I) and the like. Among these, particularly preferable compounds can be exemplified by silver nitrate, silver sulfate and the like.

Illustrative examples of the complex ion containing silver include $[Ag(S_2O_3)_2]^{3-}$, $[Ag(S_2O_3)_3]^{5-}$, $[Ag(NH_3)_2]^+$, $[Ag(CN)_2]^-$, $[Ag(CN)_3]^{2-}$, $[Ag(SCN)_2]^-$, $[Ag(SCN)_4]^{3-}$ and the like. Among these, particularly preferable complex ions can be exemplified by $[Ag(S_2O_3)_2]^{3-}$, $[Ag(S_2O_3)_3]^{5-}$ and the like.

Illustrative examples of the compound containing cobalt include cobalt chloride, cobalt nitrate, cobalt sulfate, cobalt fluoride, cobalt perchlorate, cobalt bromide, cobalt iodide, cobalt selenate, cobalt thiocyanate, cobalt acetate, ammonium cobalt sulfate, cobalt(II) potassium sulfate, hexaamminecobalt(III) chloride, pentaammineaquacobalt (III)chloride, nitropentaamminecobalt(III) chloride, dichlorotetraamminecobalt(III) chloride hemihydrate, dinitrotetraamminecobalt(III) chloride, carbonatotetraamminecobalt(III) chloride, ammonium tetranitrodiamminecobaltate(III), sodium hexanitrocobaltate (III), tris(ethylenediamine)cobalt(III) chloride trihydrate, dichlorobis(ethylenediamine)cobalt(III) chloride, potassium tris(oxalato)cobaltate(III) trihydrate, potassium hexacyanocobaltate(III), potassium (ethylenediaminetetraacetato)cobaltate(III) dihydrate, hydridotetracarbonylcobalt(I), dicarbonyl (cyclopentadienyl)cobalt(I), octacarbonyldicobalt(O), hexacarbonyl(acetylene)dicobalt(O), bis(cyclopentadienyl) cobalt(I), (cyclopentadienyl)(1,5-cyclooctadiene)cobalt(I) and the like. Among these, particularly preferable compounds can be exemplified by cobalt chloride, cobalt nitrate, cobalt sulfate and the like.

Illustrative examples of the complex ion containing cobalt include pentaammineaquacobalt ion, nitropentaamminecobalt ion, dichlorotetraamminecobalt ion, dinitrotetraamminecobalt ion, carbonatotetraamminecobalt ion, tetranitrodiamminecobalt ion, hexanitrocobalt ion, tris (ethylenediamine)cobalt ion, dichlorobis(ethylenediamine) cobalt ion, tris(oxalato)cobalt ion, hexacyanocobalt ion, (ethylenediaminetetraacetato)cobalt ion and the like.

Of the said heavy metals, the compound containing silver, the complex ion containing silver or the silver ion preferably has a concentration in the medium of $10^{-8}M$–$10^{-1}M$, and it is further preferable to adjust the concentration to be in the range of $10^{-7}M$ to $10^{-2}M$. The compound containing cobalt, the complex ion containing cobalt or the cobalt ion preferably has a concentration in the medium of $10^{-6}$–$10^{-1}M$, and it is further preferable to adjust the concentration to be in the range of $10^{-5}$ to $10^{-2}M$.

So far, there are no cases reported wherein the tissue culture of a plant producing a taxane-type diterpene is carried out in the presence of a compound containing silver, a complex ion containing silver or silver ion as an additive to the medium. Although compounds containing cobalt, or cobalt ions are contained as one of the medium components for such a medium that is generally used as a medium for the tissue culture of a plant belonging to genus Taxus, such as Linsmaier-Skoog medium, Murashige-Skoog medium, and Gamborg's B-5 medium, they are used at a concentration of $1\times10^{-7}M$–$4\times10^{-7}M$ [Growth and breeding of a wo6dy plant, edited by the latest biotechnology complete works editors committee, Nogyo Tosho, P265-268], which is a much lower concentration than those used in the method of the present invention. In the meantime, there are no cases reported wherein the tissue culture of a plant producing a taxane-type diterpene is carried out in the presence of a compound containing cobalt or cobalt ions of such a high concentration that is used in the first invention of the present application, just like the case with the above-mentioned silver compound. In addition to that, it was beyond all expectations that the amount of the taxane-type diterpene to be produced is increased by the culture carried out in the presence of such heavy metals.

According to the first invention of the present application, by amines we refer to an amine or a salt thereof. As the amines, which are the objects for the first invention of the present application, both monoamines and polyamines can be used, however, the use of polyamines is particularly preferable.

In addition to that, examples of the amines, which are the objects for the first invention of the present application, include mono, di or trialkyl amines wherein a part of hydrogen atoms in the alkyl group may be substituted by hydroxyl group, such as methyl amine, ethyl amine, dimethyl amine, diethyl amine, triethyl amine, diethanol amine, triethanol amine or a salt thereof; polymethylene diamine wherein the polymethylene moiety may be interrupted by imino group, and H in the amino group can be substituted by lower alkyl group, such as putrescine, cadaverine, spermidine, spermin, ethylenediamine, N,N-diethyl-1,3-propane diamine, triethylene tetramine, or a salt thereof; cyclic alkyl amine such as cyclopentyl amine, cyclohexyl amine or a salt thereof, or a cyclic amine such as methenamine and piperazine, or a salt thereof. Among these amines, preferable amines can be exemplified by polyamines such as putrescine [$NH_2(CH_2)_4NH_2$], cadaverine [$NH_2(CH_2)_5NH_2$], spermidine [$NH_2(CH_2)_3NH(CH_2)_4NH_2$], spermin [$NH_2(CH_2)_3NH(CH_2)_4NH(CH_2)_3NH_2$], ethylene diamine [$NH_2(CH_2)_2NH_2$], N,N-diethyl-1,3-propane diamine [$(C_2H_5)_2N(CH_2)_3NH_2$], diethylene triamine [$NH_2(CH_2)_2NH(CH_2)_2NH_2$] and the like or a salt thereof.

The said amines preferably have a concentration in the medium of $10^{-8}M–10^{-1}M$, and it is further preferable to adjust the concentration to be in the range of $10^{-7}M$ to $10^{-2}M$.

One illustrative example wherein a secondary metabolite is shown to be induced by addition of amines to the plant tissue cultures is shown in Japanese Patent Laid-Open Publication No. 4-262788 wherein indole alkaloid production is shown to be induced by addition of amines to cultured cells of Catharanthus roseus. However, there are no cases reported wherein the tissue culture of a plant producing taxane-type diterpene, which is a different plant species from that of Catharanthus roseus, was carried out in the presence of amines as an additive to the medium, and it was beyond all expectations that the amount of the taxane-type diterpene, which has a totally different biosynthetic pathway from that of the indole alkaloid, to be produced can be increased thereby.

The antiethylene agent, which is an object for the first invention of the present application is not particularly limited to any specific substance as far as it is a substance which inhibits the ethylene biosynthesis mechanism of the cultures and/or a substance which removes the ethylene remaining in the cultures or existing in the gas phase or in the medium in the culture vessel containing the cultures.

Illustrative examples of a method to inhibit the ethylene biosynthesis mechanism include a method of inhibiting the activity of an enzyme which catalyzes the conversion of S-adenosylmethionine into 1-aminocyclopropane-1-carboxylic acid, and a method of inhibiting the activity of an enzyme which catalyzes the conversion of 1-aminocyclopropane-1-carboxylic acid into ethylene, and illustrative examples of the compound having the former function include, aminoxyacetic acid, acetylsalicylic acid, Rhizobitoxine, aminoethoxyvinylglycine, methoxyvinylglycine, a-aminoisobutyric acid, 2,4-dinitrophenol and the like. They can also include a salt, an ester, an amino acid derivative and a carbohydrate derivative of the said compound.

Illustrative examples of the salt include sodium, potassium, calcium, and magnesium salts, illustrative examples of the ester include methyl, ethyl, propyl, and butyl esters, illustrative examples of the amino acid derivatives include glycine, methionine, and phenylalanine derivatives, and illustrative examples of the carbohydrate derivative include glucose and maltose derivatives. The salt, ester, amino acid derivative, carbohydrate derivative according to the present invention are not limited to the above-mentioned compounds.

Illustrative examples of the compound having the latter function include gallic acid, a salt, an ester, an amino acid derivative and a carbohydrate derivative thereof [Hiroshi Hyodo, Society of Horticulture Autumn Convention 1987 Symposium Summary, p. 122, Susumu Kuraishi, Phytohormone, Tokyo University Publication, p.111].

Illustrative examples of the salt include sodium, potassium, calcium, and magnesium salts, illustrative examples of the ester include methyl, ethyl, propyl, and butyl esters, illustrative examples of the amino acid derivatives include glycine, methionine, and phenylalanine derivatives, and illustrative examples of the carbohydrate derivatives include glucose and maltose derivatives. The salt, ester, amino acid derivative, carbohydrate derivative according to the present invention are not limited to the above-mentioned compounds.

Illustrative examples of the substance which removes the ethylene remaining in the cultures or existing in the gas phase or the medium in the culture vessel containing the cultures include 1,5-cyclooctadiene and isothiocyanic acid, a salt, an ester (such as allyl isothiocyanate and benzyl isothiocyanate), an amino acid derivative and a carbohydrate derivative thereof [Megumi Munakata, Chemical control in plants, 29(1), 89–93 (1994)].

Illustrative examples of the salt include sodium, potassium, calcium, and magnesium salts, illustrative examples of the ester include methyl, ethyl, propyl, butyl, and allyl esters, illustrative examples of the amino acid derivatives include glycine, methionine, and phenylalanine derivatives, and illustrative examples of the carbohydrate derivatives include glucose and maltose derivatives. The salt, ester, amino acid derivative, carbohydrate derivative according to the present invention are not limited to the above-mentioned compounds.

The antiethylene agent is required to have a concentration in a culture medium of $10^{-8}M–10^{-1}M$, and it is particularly preferable to control the concentration of the antiethylene agent to be in the range of $10^{-7}M$ to $10^{-2}M$.

It is known that ethylene is one of phytohormones, and involved in various physiological phenomena caused in the plant, such as growth of individium, morphogenesis, and aging. A report by Kim, Dong II et al., Biotechnol. Bioeng., 38(4), 331–339 (1991) is an illustrative example wherein ethylene is utilized for improving the productivity of the secondary metabolite by the plant. However, in all the examples wherein controlling of ethylene is utilized for improving the productivity of the secondary metabolite, it is the control of ethylene supply to the plant tissue cultures, as typically shown in the above-mentioned report, and so far there have been no cases reported in which the control to inhibit the ethylene production is utilized to improve the production of the secondary metabolite, like the method of the present invention.

In addition to that, the antiethylene agent is generally utilized as a freshness keeping agent for flowers, fruits and vegetables, however, there have been no cases reported wherein the antiethylene agent is used for the purpose of improving the production of the secondary metabolite.

Under these circumstances, the present inventors ascertained that ethylene greatly inhibits the production of the taxane-type diterpene by the tissues and the cells of the taxane-type diterpene producing plant. Accordingly, based on the above-mentioned finding, the inventors cultured the said tissue cultures in the presence of the antiethylene agent, and found out that the antiethylene agent not only controls the above-mentioned inhibition but also remarkably improves the amount of the taxane-type diterpene resulting from the cultures. There have been no cases reported wherein the production of the taxane-type diterpene is induced by culturing the tissue cultures of a plant producing taxane-type diterpene in the presence of an antiethylene agent, and it was beyond all expectations that the productivity of the above-mentioned secondary metabolite can be even increased by the method of the first invention of the present application.

Examples of the medium to be used for the first invention of the present application include those known media which have been conventionally used for the plant tissue culture, such as medium of Murashige & Skoog (1962), medium of Linsmaier Skoog (1965), Woody Plant Medium (1981), Gamborg's B-5 medium and Mitsui's M-9 medium.

A phytohormone, and if necessary a carbon source, an inorganic component, vitamins, amino acids and the like may be added as well to these media.

As a carbon source, a disaccharide such as sucrose, maltose, and lactose, a monosaccharide such as glucose, fructose and galactose, starch or a mixture of two or more kinds of such sugar sources mixed at an appropriate ratio can be utilized.

As an inorganic component, illustrative examples include phosphorus, nitrogen, potassium, calcium, magnesium, sulfur, iron, manganese, zinc, boron, copper, molybdenum, chlorine, sodium, iodine and cobalt, and these components can be added in the form of such a compound as potassium nitrate, sodium nitrate, calcium nitrate, potassium chloride, potassium monohydrogenphosphate, potassium dihydrogenphosphate, calcium chloride, magnesium sulfate, sodium sulfate, ferrous sulfate, ferric sulfate, manganese sulfate, zinc sulfate, boric acid, copper sulfate, sodium molybdate, molybdenum trioxide, potassium iodide, cobalt chloride and the like.

As the phytohormone, for example, auxin such as indoleacetic acid (IAA), naphthalenacetic acid (NAA), and 2,4-dichlorophenoxy acetic acid (2,4-D), and cytokinin such as kinetin, zeatin, and dihydrozeatin can be used.

As the vitamins, for example, biotin, thiamin (vitamin B1), pyridoxine (vitamin B6), pantothenic acid, inositol, nicotinic acid and the like can be used.

As the amino acids, for example, glycine, phenylalanine, leucine, glutamine, cysteine and the like can be added.

Generally, the carbon source in a concentration of about 1–about 30 g/l, the inorganic component in a concentration of about 0.1 $\mu$M–about 100 mM, the phytohormones in a concentration of about 0.01–about 10 $\mu$M, and the vitamins and the amino acids respectively in a concentration of about 0.1–about 100 mg/l are used.

According to the present invention, both a liquid medium and such a solid medium that contains agar and gelan gum normally in an amount of 0.1–1% can be used, however, usually a liquid medium is preferable.

According to the tissue -culture of the present invention, a piece of a tissue or a cell of a root, a growing point, a leaf, a stem, a seed, a pollen, an anther and a calyx and the like of the said plant or cultured cells which are obtained by the tissue culture thereof in the above-mentioned medium or another conventional medium can be used.

The present invention can also be applied to neoplastic cell and/or hairy-root, obtained by infecting a plant tissue with *Agrobacterium tumefaciens* or *Agrobacterium rhizogenes*.

By culturing these tissues or cells in the presence of at least one substance selected from the group consisting of jasmonic acids, compounds containing a heavy metal, complex ions containing a heavy metal, heavy metal ions, amines, and antiethylene agents, cultured tissues or cultured cells having higher taxane-type diterpene productivity than that of those obtained by the tissue culture carried out under the normal culture conditions, can be obtained.

When at least one compound selected from compounds containing a heavy metal, complex ions containing a heavy metal, heavy metal ions, amines, and antiethylene agents is used together with jasmonic acids represented by the above-mentioned general formulae (I), (II) or (III), the effect of the first inventiontof the present application can be enhanced.

Taxane-type diterpene can be fractionated from the cultures such as cultured tissues, cultured cells and culture medium, which are obtained according to the above-mentioned process, by extraction with an organic solvent such as methanol. It is also possible to recover the taxane-type diterpene continuously during culture by allowing an appropriate adsorbing agent or an organic solvent coexist in the culture medium.

One preferable example of the tissue culture according to the present invention can be illustrated as follows.

A piece of a plant body of a plant belonging to genus Taxus, such as a root, a growing point, a leaf, a stem, a seed and the like is sterilized and placed on Woody Plant Medium solidified with gelan gum, and kept at 10–35° C. for about 14–60 days so that a part of the tissue piece is changed to callus. By subculturing the callus thus obtained, the growing speed is gradually increased and stabilized callus can be obtained. By the stabilized callus, we refer to a callus which remains in callus state during culture without showing differentiation into a shoot or a root and the cells of which have uniform growing speed.

Such stabilized callus is transferred to a liquid medium, suited for the growth, such as liquid Woody Plant Medium and grown. The growing speed is further increased in the liquid medium. According to the present invention, the stabilized callus or the cells constituting the above-mentioned callus are grown in a solid medium or a liquid medium in the presence of at least one substance selected from a group consisting of jasmonic acids, compounds containing a heavy metal, complex ions containing a heavy metal, heavy metal ions, amines and antiethylene agents. And, it is also possible to fractionate the stabilized callus or the cells constituting the said callus into a plurality of layers according to the difference in their specific gravities and grow the cells contained in at least one layer in a culture medium containing at least one substance selected from the group consisting of jasmonic acids, compounds containing a heavy metal, complex ions containing a heavy metal, heavy metal ions, amines and antiethylene agents.

In a generally known method to fractionate the cells according to their specific gravities, density gradient is formed by a medium for centrifugal separation, and the cells are layered over it, then centrifugal separation is carried out.

As a medium for centrifugal separation, Ficoll, Percoll (both produced by Pharmacia LKB Biotechnology Co. Ltd.,), sucrose and cesium chloride and the like are used. In the examples including Example No.5, the density gradient was produced by the use of Ficoll, however, the medium is not particularly limited to any substance as far as it does not damage the cells.

The number of the layers forming the density gradient is not particularly restricted. The difference between the specific gravities of layers is not particularly limited and each difference in the specific gravity can be the same or different.

Accordingly, the definition of the density gradient includes a case wherein the gradient changes continuously (the condition wherein the number of the layers forming the density gradient is close to infinite, and the specific gravity difference between each layer is close to 0).

The cells can be fractionated into a plurality of layers according to the difference in their specific gravities by thus forming the density gradient, layering the cells and carrying out the centrifugal separation.

The specific gravity of the layer to be formed is normally in the range of 1.00 to 1.20 g/ml, preferably in the range of 1.03 to 1.11 g/ml. As a layer to become an object for culture, at least one layer is selected, but it is also possible to select all the layers and culture them.

When a plurality of layers are selected and cells contained in the selected layers are cultured, it is possible to culture the cells in these layers individually, but, it is also possible to mix the cells in two or more layers of the selected plurality of layers and culture them.

The cultured cells having high taxane-type diterpene productivity can be usually obtained by culturing cells contained in a layer having the specific gravity of 1.07 or less, but it is not always limited to this range, since it may fluctuate depending on the cells to be cultured or the culture conditions. There is also a tendency that the cells in a layer of a higher specific gravity, have a higher content of the taxane-type diterpene at the time when the fractionation is carried out according to the difference in the specific gravities. Accordingly, to ensure that cultured cells which produce the taxane-type diterpene at a high rate can be obtained, it is desirable that the cells in all the fractionated layers are cultured for a certain period, then the concentration of the taxane-type diterpene in the cells of each layer is measured, and the layer containing the cultured cells which produce the taxane-type diterpene at a high rate is selected from among those layers.

It is also possible to fractionate the cultured cells into a plurality of layers according to the difference in the specific gravities by preparing a medium for centrifugal separation having one particular specific gravity such as 1.07 g/ml, for example, and carrying out the centrifugal separation according to the above-mentioned method.

Furthermore, the first invention of the present application can be used together with the method of the second invention of the present application wherein the culture is carried out by controlling the oxygen concentration in a gas phase in a culture vessel to less than the oxygen concentration in the atmosphere, from the initial stage of the culture, or by controlling the dissolved oxygen concentration in a fluid medium which is in contact with the tissue or the cell to less than the saturated dissolved oxygen concentration at that temperature from the initial stage of the culture.

Here, by the initial stage of the culture, we refer to from the time when the culture was started through the 7th day after the start of the culture, and the controlling of the oxygen concentration in the gas phase in the culture vessel or the controlling of the dissolved oxygen concentration in the fluid medium which is in contact with the tissue or the cell is preferably done from the beginning of the culture. The controlling period is not particularly limited, and, the controlling under the said conditions can be done in the entire culture period, or only in a part of the entire culture period, however, it is preferable to carry out the control at least for 3 days during the entire culture period.

The oxygen concentration in the gas phase in the culture vessel is required to be controlled to 4–15%, and it is particularly preferable to control it to 6–12%. The dissolved oxygen concentration in the fluid medium is required to be controlled to 1–75% of the saturated dissolved oxygen concentration at that temperature and it is particularly preferable to control it to 10–75%.

It is also possible to combine the first invention of the present application, the second invention of the present application and the third invention of the present application all together.

According to the first invention of the present application, it is effective to add jasmonic acids when the cultured cells are in the exponential growth phase or in the stationary phase, and it is particularly preferable to add jasmonic acids in a transitional period from the exponential growth phase to the stationary phase. The same can be said of the timing of the treatment for increasing the amount of the endogenous jasmonic acids to be produced. For example, when cells are subcultured in every 21 days, the 7th–16th day is the suitable time for addition of the jasmonic acids or the treatment to increase the amount of the endogenous jasmonic acids to be produced, and when the cells in the exponential growth phase, for example those on the 7th–14th day are to be subcultured, the suitable time is immediately after the transplantation. The addition of the jasmonic acids or the treatment to increase the amount of the endogenous jasmonic acid to be produced can be done at a time, in a plurality of parts, or continuously.

It is effective to add compounds containing a heavy metal, complex ions containing a heavy metal or heavy metal ions after the beginning of the culture and before the transitional period of the cultured cells from the exponential growth phase to the stationary phase, and it is particularly preferable to add them at the beginning of the culture. The addition of the said compounds or the ions can be done at a time, or in a plurality of parts.

It is effective to add amines before the transitional period of the cells from the exponential growth phase to the stationary phase, and it is particularly preferable to add them at the beginning of the culture. The addition of said compounds can be done at a time or in a plurality of parts.

It is effective to add antiethylene agents before the transitional period of the cells from the exponential growth phase to the stationary phase, and it is particularly preferable to add them immediately after the transition to the stationary phase. The addition of the said compounds can be done at a time or in a plurality of parts.

The temperature for the tissue culture according to the first invention of the present application is usually about 10–about 35 ° C., and preferably about 23–28° C. according to the high growing speed. As for the culture period, 14–42 days are preferable.

When a liquid medium is used for the culture according to the first invention of the present application, the cultured cells can be fractionated from the culture medium after the culture is completed, by such a method as decantation or filtration and the desired taxane-type diterpene can be fractionated from the cultured cells and/or the culture medium by such a method as extraction with an organic solvent The second invention of the present application will be explained as follows.

According to the second invention of the present application, the culture of the plant means culture of a tissue or a cell of the plant, wherein the culture is carried out by a conventionally known process except that the culture is carried out by controlling the oxygen concentration in the gas phase of the culture vessel to below the atmospheric oxygen concentration from the initial stage of the culture, or by controlling the dissolved oxygen concentration in the fluid medium which is in contact with the tissue or the cell to below the saturated dissolved oxygen concentration at that temperature from the initial stage of the culture.

So far, in the culture of a plant producing the taxane-type diterpene, there has been no reports wherein the culture is carried out under such conditions that the oxygen concentration in the gas phase to be supplied to the culture vessel wherein the tissue or the cells are cultured or the dissolved oxygen concentration in the medium which is in contact with the tissue or the cells to below the atmospheric oxygen concentration or below the saturated dissolved oxygen concentration, and it was beyond all expectations that the amount of the taxane-type diterpene to be produced is increased by that.

According to the second invention of the present application, the oxygen concentration in the gas phase of the culture vessel wherein the tissue or the cells are cultured is required to be controlled to 4–15%, it is particularly preferably controlled to 6–12%. The dissolved oxygen concentration of the fluid medium which is in contact with the tissue or the cells is required to be controlled to 1–75% of the saturated dissolved oxygen concentration at that temperature, it is particularly preferably controlled to 10–75%.

Examples of a medium to be used in the second invention of the present application, include the medium conventionally known for the tissue culture of a plant, such as medium of Murashige & Skoog (1962), medium of Linsmaier Skoog (1965), Woody Plant Medium (1981), Gamborg's B-5 medium, and Mitsui's M-9 medium and the like.

A phytohormone, and if necessary a carbon source, an inorganic component, vitamins, amino acids and the like may be added as well to these media.

As a carbon source, a disaccharide such as sucrose, maltose, and lactose, a monosaccharide such as glucose, fructose and galactose, starch or a mixture of two or more kinds of such sugar sources mixed at an appropriate ratio can be utilized.

As an inorganic component, illustrative examples include phosphorus, nitrogen, potassium, calcium, magnesium, sulfur, iron, manganese, zinc, boron, copper, molybdenum, chlorine, sodium, iodine and cobalt, and these components can be added in the form of such a compound as potassium nitrate, sodium nitrate, calcium nitrate, potassium chloride, potassium monohydrogenphosphate, potassium dihydrogenphosphate, calcium chloride, magnesium sulfate, sodium sulfate, ferrous sulfate, ferric sulfate, manganese sulfate, zinc sulfate, boric acid, copper sulfate, sodium molybdate, molybdenum trioxide, potassium iodide, cobalt chloride and the like.

As the phytohormone, for example, auxin such as indoleacetic acid (IAA), naphthalenacetic acid (NAA), and 2,4-dichlorophenoxy acetic acid (2,4-D), and cytokinin such as kinetin, zeatin, and dihydrozeatin can be used.

As the vitamins, for example, biotin, thiamin (vitamin $B_1$), pyridoxine (vitamin $B_6$), pantothenic acid, inositol, nicotinic acid and the like can be used.

As the amino acids, for example, glycine, phenylalanine, leucine, glutamine, cysteine and the like can be added.

Generally, the carbon source in a concentration of about 1–about 30 g/l, the inorganic component in a concentration of about 0.1 $\mu$M–about 100 mM, the phytohormones in a concentration of about 0.01–about 10 $\mu$M, and the vitamins and the amino acids respectively in a concentration of about 0.1–about 100 mg/l are used.

According to the second invention of the present application, both a liquid medium and such a solid medium that contains agar and gelan gum normally in an amount of 0.1–1% can be used.

According to the tissue culture of the second invention of the present application, a piece of a tissue or a cell of a root, a growing point, a leaf, a stem, a seed, a pollen, an anther and a calyx and the like of the said plant or cultured cells which are obtained by the tissue culture thereof in the above-mentioned medium or another conventional medium can be used.

The second invention of the present application can also be applied to neoplastic cell and/or hairy-root, obtained by infection with *Agrobacterium tumefaciens* or *Agrobacterium rhizogenes*.

When these tissues or cells are cultured by controlling the oxygen concentration in the gas phase in the culture vessel to less than the oxygen concentration in the atmosphere, from the initial stage of the culture, or by controlling the dissolved oxygen concentration in the fluid medium which is in contact with the tissue or the cell to less than the saturated dissolved oxygen concentration at that temperature, from the initial stage of the culture, cultured tissue or the cultured cells having higher taxane-type diterpene productivity than that of those obtained by the tissue culture carried out under normal culture conditions can be obtained.

According to the second invention of the present application, the initial stage of the culture refers to from the time when the culture was started through the 7th day after the start of the culture, and the controlling of the oxygen concentration in the gas phase in the culture vessel or the controlling of the dissolved oxygen concentration in the fluid medium which is in contact with the tissue or the cell is preferably done from the beginning of the culture.

The controlling period is not particularly limited, and, the controlling under the said condition can be done in the entire culture period, or only in a part of the entire culture period, however, it is preferable to carry out the control at least for 3 days during the entire culture period.

The production method according to the second invention of the present application can be used together with a culture method carried out in the presence of various kinds of taxane-type diterpene production promoting substances to further increase the productivity of the taxane-type diterpene.

Examples of the taxane-type diterpene production promoting substance include, for example, jasmonic acids represented by the above-mentioned general formulae (I), (II) or (III), compounds containing a heavy metal, complex ions containing a heavy metal, heavy metal ions, amines and antiethylene agents to be used for the above-mentioned first invention of the present application.

Also the second invention of the present application can be also used together with the method of the third invention of the present application which will be described later in detail, wherein the cells are fractionated into a plurality of layers according to the difference in their specific gravities, and the cells contained in at least one layer are cultured.

The production method according to the second invention of the present application can be used together with both the said method according to the first invention of the present application wherein culture is carried out in the presence of the jasmonic acids and the like and the method according to the third invention of the present application wherein the cells are fractionated into a plurality of layers according to the difference in their specific gravities and cells contained in at least one layer are cultured.

Taxane-type diterpene can be fractionated from the cultures such as cultured tissues, cultured cells and culture medium, which are obtained according to the above-mentioned process, by extraction with an organic solvent such as methanol.

One preferable example of the tissue culture according to the second invention of the present application can be illustrated as follows.

A piece of a plant body of a plant belonging to genus Taxus, such as a root, a growing point, a leaf, a stem, a seed and the like is sterilized and placed on Woody Plant Medium solidified with gelan gum, and kept at 10–35° C. for about 14–60 days so that a part of the tissue piece is changed to callus. By subculturing the callus thus obtained, the growing speed is gradually increased and stabilized callus can be obtained. By the stabilized callus, we refer to a callus which remains in callus state during culture without showing differentiation into a shoot or a root and the cells of which have uniform growing speed.

Such stabilized callus is transferred to a liquid medium, suited for the growth, such as liquid Woody Plant Medium and grown. The growing speed is further increased in the liquid medium. According to the present invention, the stabilized callus or the cells constituting the above-mentioned callus is grown under the culture conditions wherein the oxygen concentration in a gas phase in a culture vessel is controlled to less than the oxygen concentration in the atmosphere from the initial stage of the culture, or the dissolved oxygen concentration in a fluid medium which is in contact with the tissue or the cell is controlled to less than the saturated dissolved oxygen concentration at that temperature, from the initial stage of the culture.

The tissue or the cell gains energy necessary for maintenance and growth of individium, by consuming oxygen (respiration). It is generally known that when a tissue or a cell is cultured, the cell mass is increased and the amount of the oxygen consumption is increased as well with the passage of culture period. Accordingly unless a ventilation gas is forcedly supplied from outside of the system, the oxygen concentration in the gas phase in the culture vessel such as a flask wherein the tissue or the cell is contained, or the dissolved oxygen concentration in the medium which is in contact with the tissue or the cell naturally decreases to a value less than the oxygen concentration in the atmosphere, or the saturated dissolved oxygen concentration at that temperature, with the passage of culture period.

The present invention is different from the above-mentioned finding on the point that the culture is carried out by actively controlling the oxygen concentration in the gas phase in the culture vessel which contains the tissue or the cell or the dissolved oxygen concentration in the culture medium to less than the oxygen concentration in the atmosphere or the saturated dissolved oxygen concentration at that temperature.

In one illustrative process to enhance the effect of the present invention, the oxygen concentration in the gas phase in the culture vessel or the dissolved oxygen concentration in the fluid medium is previously controlled to less than the oxygen concentration in the atmosphere or the saturated dissolved oxygen concentration at that temperature, prior to the subculture of the tissue or the cell in the culture vessel.

The controlling period is not particularly limited as mentioned above, however, it is preferable to carry out the control at least for 3 days during the entire culture period.

In addition to that, the controlling method is not particularly limited to any as far as it is a method wherein the oxygen concentration in the gas phase in the culture vessel which contains the tissue or the cell, or the dissolved oxygen concentration in the fluid medium which is in contact with the tissue or the cell, can be controlled to less than the oxygen concentration in the atmosphere or the saturated dissolved oxygen concentration at that temperature, and in some examples of such method, a gas having a controlled oxygen concentration, which is obtained by mixing an air with nitrogen and the like to lower the oxygen concentration, is directly sent into the gas phase in the culture vessel or the culture medium, or such a gas is directly sent into the culture medium outside of the culture vessel, i.e. in an aeration tank and the like, then the culture medium is poured into the culture vessel, or a gas such as air to be supplied to the culture vessel is directly sent into the gas phase or the culture medium by controlling the feed speed, or such a gas is directly sent into the culture medium outside of the culture vessel, i.e. in an aeration tank and the like then the culture medium is poured into the culture vessel, or the culture vessel is placed under low oxygen atmosphere to carry out culture or the culture is carried out in the presence of an oxygen adsorbing agent.

The temperature for the tissue culture according to the present invention is usually about 10–about 35° C., and preferably about 23–28 ° C. according to the high growing speed. As for the culture period, 14–42 days are preferable.

When a liquid medium is used for the culture according to the present invention, the cultured cells can be fractionated from the culture medium after the culture is completed by such a method as decantation or filtration and the desired taxane-type diterpene can be fractionated from the cultured cells and/or the culture medium by such a method as extraction with an organic solvent. It is also possible to recover the desired compound continuously during the culture by allowing an adsorbing agent or an appropriate organic solvent coexist in the culture system.

The third invention of the present application will be explained as follows.

According to the third invention of the present application, a layer containing the cultured cells, which shall show high taxane-type diterpene productivity after being cultured, can be exemplified by a layer having the specific gravity of 1.07 or less.

In a generally known method to fractionate the cells according to their specific gravities, a density gradient is formed by a medium for centrifugal separation, and the cells are layered over it, then centrifugal separation is carried out.

As a medium for centrifugal separation, Ficoll, Percoll (both produced by Pharmacia LKB Biotechnology Co. Ltd.,), sucrose and cesium chloride and the like are used. In Examples, the density gradient was produced by the use of Ficoll, however, the medium is not particularly limited to any substance as far as it does not damage the cells. Ficoll has been used for separation of cell granules and the like (Hess, R. et al., Nature 208 (1965), 856–858) or separation of animal cells (Walder, I. A. et al., Proc. Soc. exptl. Biol. Med., 112(1963) 494–496) and the like.

The number of the layers forming the density gradient is not particularly limited.

In Examples, a density gradient wherein the difference of the specific gravity between each layer is 0.02 is formed by the layers having the specific gravity of 1.03, 1.05, 1.07, 1.09 and 1.11 (g/ml), however, the difference of the specific gravity is not limited to this value, and the difference of the specific gravity between each layer can be the same or different.

Accordingly, the definition of the density gradient includes a case wherein the gradient changes continuously (the condition wherein the number of the layers forming the density gradient is close to infinite, and the difference of the specific gravity between each layer is close to 0).

The cells can be fractionated into a plurality of layers according to the difference in their specific gravities by thus forming the density gradient, layering the cells and carrying out the centrifugal separation.

The specific gravity of the layer to be formed is normally in the range of 1.00 to 1.20 g/ml, preferably in the range of 1.03 to 1.11 g/ml. As a layer to become an object for culture, at least one layer is selected, but it is also possible to select all the layers and culture them.

When a plurality of layers are selected and cells contained in the selected layers are cultured, it is possible to culture the cells in these layers individually, but, it is also possible to mix the cells in two or more layers of the selected plurality of layers and culture them.

The cultured cells having high taxane-type diterpene productivity can be usually obtained by culturing cells contained in a layer having the specific gravity of 1.07 or less, but, it is not always limited to this range, since it may fluctuate depending on the cells to be cultured or the culture conditions. There is also a tendency that the cells in a layer of a higher specific gravity, have a higher content of the taxane-type diterpene at the time when the fractionation is carried out according to the difference in the specific gravities. Accordingly, to ensure that cultured cells which produce the taxane-type diterpene at a high rate can be obtained, it is desirable that the cells in all the fractionated layers are cultured for a certain period, then the concentration of the taxane-type diterpene in the cells of each layer is measured, and the layer containing the cultured cells which produce the taxane- type diterpene at a high rate is selected from among those layers.

So far, there have been no cases reported wherein the cultured cells of a plant producing the taxane-type diterpene are cultured after they are fractionated according to the specific gravity of the cells, and it was beyond all expectations that the cells can be fractionated into layers of cells each having different taxane-type diterpene productivity, by the difference of the specific gravities, and that the cells which produce the taxane-type diterpene at a high rate can be obtained by culture of cells which are contained in a layer having the specific gravity of 1.07 or less, and whose taxane-type diterpene content is not so high at the time when they are fractionated.

According to the present invention, it is also possible to fractionate the cultured cells into a plurality of layers according to the difference in the specific gravities by preparing a medium for centrifugal separation having one particular specific gravity such as 1.07 g/ml, for example, and carrying out the centrifugal separation according to the above-mentioned method.

The culture medium to be used for the present invention includes typical culture medium components. As such a component, an inorganic component and a carbon source are typically used, and phytohormones, vitamins, and if necessary, amino acids can be added as well. As a carbon source, a disaccharide such as sucrose, maltose, and lactose, monosaccharide such as glucose, fructose and galactose, starch or a mixture of two or more kinds of such sugar sources mixed at an appropriate ratio can be utilized.

As an inorganic component, illustrative examples include phosphorus, nitrogen, potassium, calcium, magnesium, sulfur, iron, manganese, zinc, boron, copper, molybdenum, chlorine, sodium, iodine and cobalt, and these components can be added in the form of such a compound as potassium nitrate, sodium nitrate, calcium nitrate, potassium chloride, potassium monohydrogenphosphate, potassium dihydrogenphosphate, calcium chloride, magnesium sulfate, sodiumsulfate, ferrous sulfate, ferricsulfate, manganese sulfate, zinc sulfate, boric acid, copper sulfate, sodium molybdate, molybdenum trioxide, potassium iodide, cobalt chloride and the like.

As the phytohormone, for example, auxin such as indoleaceacid (IAA), naphthalenacetic acid (NAA), 2,4-dichlorophenoxy acetic acid (2,4-D), and cytokinin such as kinetin, zeatin, dihydrozeatin can be used.

As the vitamins, for example, biotin, thiamin (vitamin $B_1$), pyridoxine (vitamin $B_6$), pantothenic acid, inositol, nicotinic acid and the like can be used.

As the amino acids, for example, glycine, phenylalanine, leucine, glutamine, cysteine and the like can be added.

Generally, the inorganic component in a concentration of about 0.1 μM–about 100 mM, the carbon source in a concentration of about 1–about 30 g/l, the phytohormone in a concentration of about 0.01–about 10 μM, and the vitamins and the amino acids respectively in a concentration of about 0.1–about 100 mg/l are used.

Examples of a medium to be used for the present invention include those known media which have been conventionally used for the plant tissue culture, such as Medium of Murashige & Skoog (1962), medium of Linsmaier Skoog (1965), Woody Plant Medium (1981), Gamborg's B-5 medium and Mitsui's M-9 medium to which the above-mentioned phytohormone, and if necessary, the above-mentioned carbon source, vitamins and amino acids are added.

According to the present invention, both a liquid medium and such a solid medium that contains agar and gelan gum normally in an amount of 0.1–1% can be used, however, usually a liquid medium is preferable.

According to the tissue culture of the present invention, a piece of a tissue or a cell of a root, a growing point, a leaf, a stem, a seed, a pollen, an anther and a calyx and the like of the said plant, or cultured cells which are obtained by the tissue culture thereof in the said medium or another conventional medium can be used.

By fractionating these cells into particular specific gravity ranges then culturing them according to the present invention, cultured cells having higher taxane-type diterpene productivity, in comparison with those in the control area wherein no fractionation was carried out, can be obtained. The taxane-type diterpene can be fractionated from these cultured cells by extraction with an organic solvent such as methanol.

One preferable example of the tissue culture according to the present invention can be illustrated as follows.

A piece of a plant body of a plant belonging to genus Taxus, such as a root, a growing point, a leaf, a stem, a seed and the like is sterilized and placed on Woody Plant Medium solidified with gelan gum, and kept at 10–35° C. for 14–60 days so that a part of the tissue piece is changed to callus. By subculturing the callus thus obtained, the growing speed is gradually increased and stabilized callus can be obtained. By the stabilized callus, we refer to a callus which remains in callus state during culture without showing differentiation into a shoot or a root and the cells of which have uniform growing speed.

Such stabilized callus is transferred to a liquid medium, suited for the growth, such as liquid Woody Plant Medium and grown. The growing speed is further increased in the liquid medium.

The temperature for the tissue culture according to the present invention is usually about 10–about 35° C., and preferably about 23–28° C. according to the high growing speed. As for the culture period, 14–42 days are preferable.

When a liquid medium is used for the culture according to the present invention, the cultured cells can be fractionated from the culture medium after the culture is completed, by such a method as decantation or filtration and the desired taxane-type diterpene can be fractionated from this by such a method as extraction with an organic solvent.

According to the first invention and the second invention of the present application, taxane-type diterpene can be easily obtained in large quantity.

According to the third invention of the present application, cultured cells which produce taxane-type diterpene at a high rate can be obtained with a simple operation.

When the first, second or third invention of the present application is to be industrially executed, the efficiency can be further increased by employing the following fourth, fifth, sixth or seventh invention of the present application in an independent form or in a combined form.

That means, it is necessary to supply a gas containing oxygen to a culture liquid to culture tissues or cells of a plant which produces taxane-type diterpene. Normally, air is used for this purpose, however, after an intensive study, the present inventors found that the taxane-type diterpene production can be efficiently carried out by the use of a gas containing 0.03–10%, preferably 0.1–5% of carbon dioxide, as a gas to be introduced to a tank for culturing the tissues or the cells of the plant producing the taxane-type diterpene, and completed the fourth invention of the present application.

The present inventors also found that the productivity of the taxane-type diterpene in the cultures can be remarkably improved and the fluctuation of the taxane-type diterpene productivity due to the subculture can be controlled by carrying out a two-stage culture of the tissue or the cell of the plant producing the taxane-type diterpene, comprising a first stage using a medium to which an oxidizing agent or a water soluble organic compound containing oxygen is added for obtaining the tissues or the cells which is activated for production of the taxane-type diterpene in the subsequent stage, and a second stage which is carried out such conditions that promote the production of the taxane-type diterpene, and completed the fifth invention of the present application. Here, examples of the oxidizing agent include peroxodisulfates such as potassium peroxodisulfate and hydrogen peroxide, and examples of the water soluble organic compound containing oxygen include dimethyl formamide, dimethyl sulfoxide, and ethylene glycol and the like. The total concentration of the above-mentioned additive in the culture medium is preferably $10^{-6}M$–$10^{-1}M$ immediately after the addition, and it is further preferable to control the concentration to be in the range of $10^{-5}M$ to $10^{-2}M$.

The present inventors also found that the high density culture of the tissue or the cell of the plant producing the taxane-type diterpene can be carried out by inoculating the tissues or the cells in a culture medium containing a saccharide in a concentration of 2–50 g/l, preferably 10–30 g/l, and/or nitrate ion in a concentration of 2–50 mmol/l, preferably 10–30 mmol/l, then by adding a nutrient source solution containing the saccharide in an amount of 0.2–5 g/l, preferably 0.5–3 g/l, and/or nitrate ion in an amount of 0.2–5 mmol/l, preferably 0.5–3 mmol/l per day with respect to the initial volume of the said culture medium, continuously or intermittently to the culture medium, thereby the taxane-type diterpene production volume per culture vessel can be remarkably increased and completed the sixth invention of the present application. Here, by the density, we refer to a cell mass per volume of the culture solution in the culture vessel, which is shown in terms of dry cell mass (g) per liter of the culture solution. According to the sixth invention of the present application, it is preferable to carry out culture while the culture medium is renewed by adding the nutrient source solution and simultaneously separating and removing the same volume of the medium from the tissues or the cells and to recover the taxane-type diterpene from at least one selected from the resulting cultures, the medium recovered by removal during the culture, and the medium obtained at the end of the culture. The sixth invention of the present application is particularly effective in improving the taxane-type diterpene productivity in the high density culture wherein the density of the tissue or the cell of the above-mentioned plant at the start of the culture with respect to the medium volume is 50 g fresh weight/l or higher.

Furthermore, though the culture is normally finished when the cells of high density are obtained, the present inventors achieved, through the intensive study, the continuous culture by continuing the culture while the cells are removed, and after further examination, finally completed a continuous culture method, which is the seventh invention of the present application. That means, the taxane-type diterpene can be produced with such a high rate that could be hardly attained with the conventional process, by adding the fresh medium continuously or intermittently in such a way that the specific renewing ratio defined by the dimensionless number $F=V_f/V/\mu$ (wherein, V is the total volume of the culture medium in a culture tank, $V_f$ is the feed speed of the fresh medium, and $\mu$ is the specific growth rate of the tissues or the cells) is in the range of 0.1 to 10, and by recovering the taxane-type diterpene from the culture medium containing the tissues or the cells which is continuously or intermittently taken out from the tank and/or the culture solution which does not contain the tissue nor the cell and which is continuously or intermittently taken out from the tank, and completed the seventh invention of the present application. It is further preferable to set the specific renewing ratio of the culture medium, F, to 0.5–5. The saccharide concentration in the culture solution is preferably 5–40 g/l, and the nitrate ion concentration in the culture solution is preferably 10–40 mmol/l. The present invention can be effective with the cell density in terms of fresh cell weight per litter of 50–500 g, however, the higher the density is as far as it is in a range wherein extremely vigorous stirring is not required, the more efficiently the taxane-type diterpene can be produced, thus the preferable density is 200 g or higher per liter.

In order to combine the above-mentioned fourth, fifth, sixth, or seventh invention of the present application with the above-mentioned third invention of the present application, the cells obtained according to the third invention of the present application can be cultured according to the fourth, fifth, sixth or seventh invention of the present application to produce the desired taxane-type diterpene.

BRIEF DESCRIPTION OF DRAWINGS

1 Air feed pipe
2 Nitrogen feed pipe
3 Culture vessel
4 Sparger for supplying oxygenic gas
5 Electrode for dissolved oxygen
6 Dissolved oxygen concentration controller
7 Vent
8 Valve
9 Oxygen flow control valve
10 Air filter
11 Impeller

Figure 1:
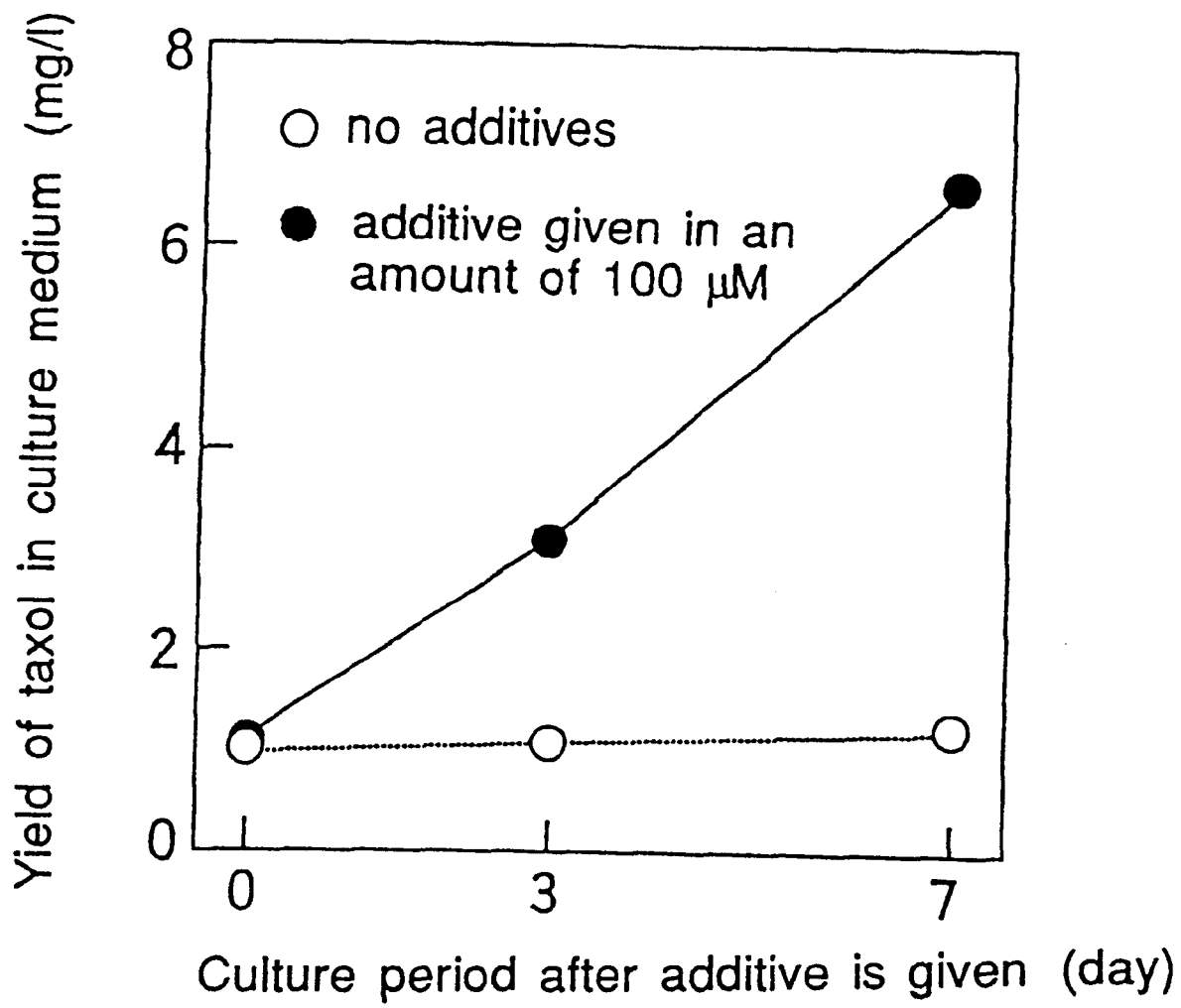
FIG. 1 is a graph showing the change of the yield of the taxol in the culture medium after adding 100 $\mu$M of methyl jasmonate.

12 Medium feed pipe
13 Medium feed opening
14 Opening with a filter for taking out culture medium alone (the culture medium containing no tissues nor cells)
15 Culture medium outlet pipe
16 Sparger for supplying oxygenic gas
17 Impeller
18 Culture mixture (the culture solution containing tissues or cells) discharge pipe
19 Pressurized fluid inlet
a, b, c, d and e Valves

BEST MODE FOR CARRYING OUT THE INVENTION

The invention will be further illustrated with the following examples and comparative examples, however, these examples are not to be construed to limit the scope of the invention.

Example 1

A part of stem of *Taxus baccata* LINN which had been previously sterilized with 2% antiformin solution or 70% ethanol solution and the like, was placed on solid Woody Plant Medium (containing gelan gum of 0.25% by weight) to which naphthalenacetic acid had been added to give the concentration of $10^{-5}$M, and static culture was carried out at 25° C. in a dark place to provide callus of Taxus baccata LINN. One gram (fresh weight) of the callus was inoculated to an Erlenmeyer flask containing 20 ml of liquid Woody Plant Medium to which the above-mentioned component was added to give the same concentration and shake culture was carried out with a rotary shaker (amplification of 25 mm, 120 rpm) and the callus was subcultured in every 21 days to accelerate the growth rate thereof.

One gram (fresh weight) of the cultured cells thus obtained was inoculated to an Erlenmeyer flask containing 20 ml of liquid Woody Plant Medium to which the above-mentioned component was added to give the same concentration, and shake culture was carried out at 25° C. for 14 days. On the 14th day after starting the culture, methyl ester of tuberonic acid (which is a compound represented by the general formula (I), wherein $R^{1a}$, $R^{1b}$, $R^{1c}$, $R^{1d}$, $R^{1e}$, $R^{1f}$, $R^2$, $R^3$, $R^4$, $R^5$, and $R^{6a}$ are hydrogen atoms, $R^{6b}$ is hydroxyl group, $R^7$ is methoxy group, n is 1 and $C^3$ and $C^4$ have a double bond between them) was added as the compound represented by the general formula (I) to give the final concentration of 0.01–1000 μM, and the culture was further carried out for another 7 days.

After completing the culture, cultured cells of *Taxus baccata* LINN were harvested by filtration and lyophilized, then the dry weight was measured to obtain the yield of the cultured cells per liter of the liquid medium. Taxane-type diterpenes were extracted from the dried callus with methanol and the like, and they were determined by comparing with standard taxol, cephalomannine, and baccatin III using high performance liquid chromatography to measure the yields of the taxane-type diterpenes. The results are shown in Table 1.

Comparative Example 1

The procedure of Example 1 was carried out except that the methyl ester of tuberonic acid was not added. The results are shown in Table 1.

Example 2

The procedure of Example 1 was carried out except that the methyl ester of tuberonic acid was added successively a total of 4 times in every two days starting from the 7th day after starting the culture (to give the final concentration of 25 μM each time, and to give the total concentration of 100 μM). The results are shown in Table 1.

Example 3

The procedure of Example 1 was carried out except that 100 μM of the methyl ester of tuberonic acid was added on the first day after starting the culture then the culture was further carried out for another 20 days. The results are shown in Table 1.

Example 4

The procedure of Example 1 was carried out except that 100 μM of the methyl ester of tuberonic acid was added on the 7th day after starting the culture and the culture was further carried out for another 14 days. The results are shown in Table 1.

TABLE 1

| | concentration of methyl tuberonate (μM) | cell yield (g/l) | yield *) of baccatin III (mg/l) | yield *) of taxol (mg/l) | yield *) of cephalomannine (mg/l) |
|---|---|---|---|---|---|
| Comparative Example 1 | 0 | 14.3 | 0.4 | 3.5 | 1.2 |
| Example 1 | 0.01 | 14.3 | 0.4 | 4.6 | 1.3 |
| Example 1 | 0.1 | 13.5 | 0.5 | 5.5 | 1.5 |
| Example 1 | 1 | 13.2 | 0.7 | 6.9 | 1.8 |
| Example 1 | 10 | 13.0 | 0.9 | 14.8 | 2.2 |
| Example 1 | 100 | 12.7 | 12.2 | 16.5 | 2.4 |
| Example 1 | 250 | 12.5 | 14.5 | 21.1 | 2.2 |
| Example 1 | 500 | 11.6 | 15.0 | 10.6 | 2.3 |
| Example 1 | 1000 | 7.5 | 1.2 | 3.9 | 1.8 |

TABLE 1-continued

|  | concentration of methyl tuberonate ($\mu$M) | cell yield (g/l) | yield *) of baccatin III (mg/l) | yield *) of taxol (mg/l) | yield *) of cephalomannine (mg/l) |
|---|---|---|---|---|---|
| Example 2 | 100 (25 × 4) | 12.9 | 13.5 | 22.5 | 2.3 |
| Example 3 | 100 | 7.1 | 1.0 | 4.0 | 1.3 |
| Example 4 | 100 | 12.5 | 10.5 | 15.6 | 2.1 |

*) The yield was calculated based on the total amount of production (in the cell + in the medium).

Example 5

The cells with accelerated growth rate obtained by the method of Example 1 were fractionated firstly by a stainless steel mesh and cell clusters having the size of 250–840 $\mu$m were obtained. A medium having a specific gravity of 1.07 (g/ml) was produced by the use of Ficoll and the above-mentioned cells were layered over it and centrifuged at 700 rpm for 6 minutes. The cells were fractionated into two layers according to the difference of the specific gravity. The cells contained in the layer of 1.07 g/ml or less were fractionated and washed with 2% sucrose solution three times or more, to wash off Ficoll. After the washing, 1 g (fresh weight) of the cells was transferred to an Erlenmeyer flask containing 20 ml of liquid Woody Plant Medium and shake culture was carried out at 25° C. for 14 days. On the 14th day after starting the culture, methyl ester of tuberonic acid was added to it to give the final concentration of 250 $\mu$M, and the culture was further carried out for another 7 days. After completing the culture, the procedure of Example 1 was carried out. The results are shown in Table 2. The productivity of the taxane-type diterpenes could be greatly improved by the combination of the selection of cells having a particular specific gravity and the addition of the methyl ester of tuberonic acid.

Comparative Example 2

The procedure of Example 5 was carried out except that the methyl ester of tuberonic acid was not added. The results are shown in Table 2.

TABLE 2

|  | concentration of methyl tuberonate ($\mu$M) | cell yield (g/l) | yield *) of baccatin III (mg/l) | yield *) of taxol (mg/l) | yield *) of cephalomannine (mg/l) |
|---|---|---|---|---|---|
| Comparative Example 2 | 0 | 14.2 | 0.5 | 5.4 | 1.5 |
| Example 5 | 250 | 12.2 | 17.4 | 28.3 | 3.1 |

*) The yield was calculated based on the total amount of production (in the cell + in the medium).

Example 6

250 $\mu$M of methyl ester of tuberonic acid was added to cultured cells of *Taxus brevifolia* NUTT obtained on the 14th day after starting the culture by the method of Example 1, and the culture was further carried out for another 7 days. After completing the culture, the procedure of Example 1 was carried out. The results are shown in Table 3.

Comparative Example 3

The procedure of Example 6 was carried out except that methyl ester of tuberonic acid was not added. The results are shown in Table 3.

Example 7

The procedure of Example 6 was carried out except that cultured cells of T. media were used. The results are shown in Table 3.

Comparative Example 4

The procedure of Example 7 was carried out except that the methyl ester of tuberonic acid was not added. The results are shown in Table 3.

TABLE 3

|  | concentration of methyl tuberonate ($\mu$M) | cell yield (g/l) | yield *) of baccatin III (mg/l) | yield *) of taxol (mg/l) | yield *) of cephalomannine (mg/l) |
|---|---|---|---|---|---|
| Comparative Example 3 | 0 | 12.5 | 0.1 | 0.2 | 0.2 |
| Example 6 | 250 | 10.0 | 1.4 | 3.3 | 0.5 |
| Comparative Example 4 | 0 | 13.6 | 0.2 | 0.3 | 0.1 |
| Example 7 | 250 | 9.5 | 10.4 | 5.4 | 0.5 |

*) The yield was calculated based on the total amount of production (in the cell + in the medium).

Example 8

A part of stem of *Taxus baccata* LINN which had been previously sterilized with 2% antiformin solution or 70% ethanol solution and the like, was placed on solid Woody Plant Medium (containing gelan gum of 0.25% by weight) to which naphthalenacetic acid had been added to give the concentration of $10^{-5}$M, and static culture was carried out at 25° C. in a dark place to provide callus of Taxus baccata LINN. One gram (fresh weight) of the callus was inoculated to an Erlenmeyer flask containing 20 ml of liquid Woody Plant Medium to which the above-mentioned component was added to give the same concentration and shake culture was carried out with a rotary shaker (amplification of 25 mm, 120 rpm) and the callus was subcultured in every 21 days to accelerate the growth rate thereof.

One gram (fresh weight) of the cultured cells thus obtained was inoculated to an Erlenmeyer flask containing 20 ml of liquid Woody Plant Medium to which the above-mentioned component was added to give the same concentration, and shake culture was carried out at 25° C. for 14 days. On the 14th day after starting the culture, methyl ester of cucurbic acid (which is a compound represented by the general formula (II) wherein $R^{1a}, R^{1b}, R^{1c}, R^{1d}, R^{1e}, R^{1f}, R^2, R^3, R^4, R^5$, and $R^6$ are hydrogen atoms, $R^7$ is methoxy group, n is 1 and $C^3$ and $C^4$ have a double bond between them) was added as one of jasmonic acids to give the final concentration of 0.01–1000 $\mu$M, and the culture was further carried out for another 7 days.

After completing the culture, cultured cells of *Taxus baccata* LINN were harvested by filtration and lyophilized, then the dry weight was measured to. obtain the yield of the cultured cells per liter of the liquid medium. Taxane-type diterpenes were extracted from the dried callus with methanol and the like, and they were determined by comparing with standard taxol, cephalomannine, and baccatin III using high performance liquid chromatography to measure the yields of the taxane-type diterpenes. The results are shown in Table 4.

Comparative Example 5

The procedure of Example 8 was carried out, except that the methyl ester of cucurbic acid was not added. The results are shown in Table 4.

Example 9

The procedure of Example 8 was carried out except that the methyl ester of cucurbic acid was added successively a total of 4 times in every two days starting from the 7th day after starting the culture (to give the final concentration of 25 μM each time, and to give the total concentration of 100 μM). The results are shown in Table 4.

Example 10

The procedure of Example 8 was carried out except that 100 μM of the methyl ester of cucurbic acid was added on the first day after starting the culture then the culture was further carried out for another 20 days. The results are shown in Table 4.

Example 11

The procedure of Example 8 was carried out except that 100 μM of the methyl ester of cucurbic acid was added on the 7th day after starting the culture and the culture was further carried out for another 14 days. The results are shown in Table 4.

TABLE 4

| | concentration of methyl cucurbate (μM) | cell yield (g/l) | yield *) of baccatin III (mg/l) | yield *) of taxol (mg/l) | yield *) of cephalomannine (mg/l) |
|---|---|---|---|---|---|
| Comparative Example 5 | 0 | 11.3 | 0.2 | 3.3 | 2.4 |
| Example 8 | 0.01 | 11.3 | 0.3 | 4.3 | 2.6 |
| Example 8 | 0.1 | 11.1 | 0.3 | 5.4 | 3.1 |
| Example 8 | 1 | 10.4 | 0.3 | 6.7 | 3.3 |
| Example 8 | 10 | 10.4 | 0.5 | 11.3 | 4.0 |
| Example 8 | 100 | 9.8 | 7.2 | 15.7 | 4.4 |
| Example 8 | 250 | 9.6 | 10.6 | 17.7 | 5.3 |
| Example 8 | 500 | 9.3 | 12.0 | 13.1 | 3.0 |
| Example 8 | 1000 | 5.7 | 1.2 | 4.2 | 2.8 |
| Example 9 | 100 (25 × 4) | 10.5 | 14.6 | 18.2 | 4.1 |
| Example 10 | 100 | 6.1 | 0.8 | 3.9 | 2.8 |
| Example 11 | 100 | 9.5 | 8.4 | 16.8 | 4.1 |

*) The yield was calculated based on the total amount of production (in the cell + in the medium).

Example 12

The cells with accelerated growth rates obtained by the method of Example 8 were fractionated firstly by a stainless steel mesh and cell clusters having the size of 250–840 μm were obtained. A medium having a specific gravity of 1.07 (g/ml) was produced by the use of Ficoll and the above-mentioned cells were layered over it and centrifuged at 700 rpm for 6 minutes. The cells were fractionated into two layers according to the difference of the specific gravity. The cells contained in the layer of 1.07 g/ml or less were fractionated and washed with 2% sucrose solution three times or more, to wash off Ficoll. After the washing, 1 g (fresh weight) of the cells was inoculated to an Erlenmeyer flask containing 20 ml of liquid Woody Plant Medium and shake culture was carried out at 25° C. for 14 days. On the 14th day after starting the culture, methyl ester of cucurbic acid was added to it to give the final concentration of 250 μM, and culture was further carried out for another 7 days. After completing the culture, the procedure of Example 8 was carried out. The results are shown in Table 5. The productivity of the taxane-type diterpenes could be greatly improved by the combination of the selection of cells having a particular specific gravity and the addition of the methyl ester of cucurbic acid.

Comparative Example 6

The procedure of Example 12 was carried out except that the methyl ester of cucurbic acid was not added. The results are shown in Table 5.

TABLE 5

| | concentration of methyl cucurbate (μM) | cell yield (g/l) | yield *) of baccatin III (mg/l) | yield *) of taxol (mg/l) | yield *) of cephalomannine (mg/l) |
|---|---|---|---|---|---|
| Comparative Example 6 | 0 | 11.5 | 0.3 | 4.3 | 2.8 |
| Example 12 | 250 | 9.7 | 22.2 | 29.7 | 3.8 |

*) The yield was calculated based on the total amount of production (in the cell + in the medium).

Example 13

250 μM of methyl ester of cucurbic acid was added to cultured cells of *Taxus brevifolia* NUTT obtained on the 14th day after starting the culture by the method of Example 8, and the culture was further carried out for another 7 days. After completing the culture, the procedure of Example 8 was carried out. The results are shown in Table 6.

Comparative Example 7

The procedure of Example 13 was carried out except that methyl ester of cucurbic acid was not added. The results are shown in Table 6.

Example 14

The procedure of Example 13 was carried out except that cultured cells of T. media were used. The results are shown in Table 6.

Comparative Example 8

The procedure of Example 14 was carried out except that the methyl ester of cucurbic acid was not added. The results are shown in Table 6.

TABLE 6

| | concentration of methyl cucurbate (μM) | cell yield (g/l) | yield *) of baccatin III (mg/l) | yield *) of taxol (mg/l) | yield *) of cephalomannine (mg/l) |
|---|---|---|---|---|---|
| Comparative Example 7 | 0 | 12.5 | 0.1 | 0.2 | 0.2 |
| Example 13 | 250 | 11.0 | 1.2 | 1.3 | 0.3 |
| Comparative Example 8 | 0 | 13.6 | 0.2 | 0.3 | 0.1 |
| Example 14 | 250 | 12.3 | 5.2 | 3.9 | 0.2 |

*) The yield was calculated based on the total amount of production (in the cell + in the medium).

Example 15

A part of stem of *Taxus baccata* LINN which had been previously sterilized with 2% antiformin solution or 70% ethanol solution and the like, was placed on solid Woody Plant Medium (containing gelan gum of 0.25% by weight)

to which naphthalenacetic acid had been added to give the concentration of $10^{-5}$M, and static culture was carried out at 25° C. in a dark place to provide callus of Taxus baccata LINN. One gram (fresh weight) of the callus was inoculated to an Erlenmeyer flask containing 20 ml of liquid Woody Plant Medium to which the above-mentioned component was added to give the same concentration and shake culture was carried out with a rotary shaker (amplification of 25 mm, 120 rpm) and the callus was subcultured in every 21 days to accelerate the growth rate thereof.

One gram (fresh weight) of the cultured cells thus obtained was inoculated to an Erlenmeyer flask containing 20 ml of liquid Woody Plant Medium to which the above-mentioned component was added to give the same concentration, and shake culture was carried out at 25° C. for 14 days. On the 14th day after starting the culture, methyl ester of jasmonic acid (which is a compound represented by the general formula (III) wherein $R^{1a}$, $R^{1b}$, $R^{1c}$, $R^{1d}$, $R^{1e}$, $R^{1f}$, $R^2$, $R^3$, $R^4$, $R^5$, and $R^6$ are hydrogen atoms, $R^7$ is methoxy group, n is 1 and $C^3$ and $C^4$ have a double bond between them, 90% of which is in the trans-form and 10% of which is in the cis-form) was added as one of jasmonic acids to give the final concentration of 0.01–1000 $\mu$M, and the culture was further carried out for another 7 days.

After completing the culture, cultured cells of Taxus baccata LINN were harvested by filtration and lyophilized, then the dry weight was measured to obtain the yield of the cultured cells per liter of the liquid medium. Taxane-type diterpenes were extracted from the dried callus with methanol and the like, and they were determined by comparing with standard taxol, cephalomannine, and baccatin III using high performance liquid chromatography to measure the yields of the taxane-type diterpenes. The results are shown in Table 7.

Comparative Example 9

The procedure of Example 15 was carried out except that the methyl ester of jasmonic acid was not added. The results are shown in Table 7.

Example 16

The procedure of Example 15 was carried out except that the methyl ester of jasmonic acid was added successively a total of 4 times in every two days starting from the 7th day after starting the culture (to give the final concentration of 25 $\mu$M each time, and to give the total concentration of 100 $\mu$M). The results are shown in Table 7.

Example 17

The procedure of Example 15 was carried out except that 100 $\mu$M of the methyl ester of jasmonic acid was added on the first day after starting the culture then the culture was further carried out for another 20 days. The results are shown in Table 7.

Example 18

The procedure of Example 15 was carried out except that 100 $\mu$M of the methyl ester of jasmonic acid was added on the 7th day after starting the culture and the culture was further carried out for another 14 days. The results are shown in Table 7.

Example 19

The procedure of Example 15 was carried out except that jasmonic acid (which is a compound represented by the general formula (III) wherein $R^{1a}$, $R^{1b}$, $R^{1c}$, $R^{1d}$, $R^{1e}$, $R^{1f}$, $R^2$, $R^3$, $R^4$, $R^5$, and $R^6$ are hydrogen atoms, $R^7$ is hydroxy group, n is 1 and $C^3$ and $C^4$ have a double bond between them; 90% of which is in the trans-form and 10% of which is in the cis-form) was added as one of jasmonic acids to give the final concentration of 0.01–1000 $\mu$M. The results are shown in Table 8.

Comparative Example 10

The procedure of Example 19 was carried out except that the methyl ester of jasmonic acid was not added. The results are shown in Table 8.

Example 20

Figure 2:
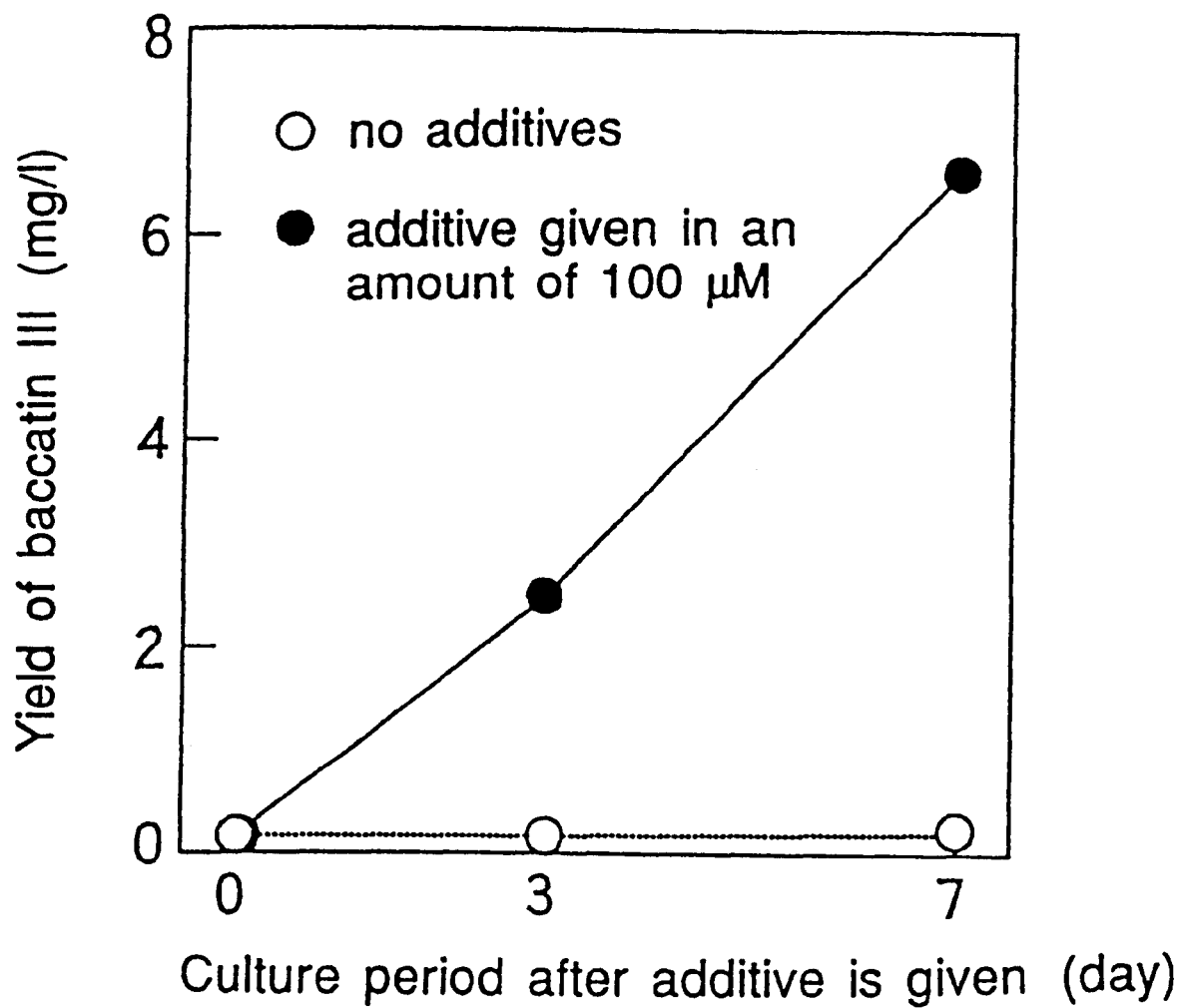
FIG. 2 is a graph showing the change of the yield of the baccatin III in the culture medium after adding 100 $\mu$M of methyl jasmonate.

The analytical results of taxane-type diterpenes existed in the culture medium of Example 15 prior to the addition of 100 $\mu$M of methyl jasmonate, on the third day after the addition, and on the 7th day after the addition, are shown in FIG. 1 and FIG. 2. On the 7th day of the culture, about half of the taxol and about 70% of the baccatin III were leaked in the medium.

Comparative Example 11

The procedure of Example 20 was carried out except that the methyl ester of jasmonic acid was not added. The results are shown in FIG. 1 and FIG. 2.

Example 21

The cells with accelerated growth rate obtained by the method of Example 15 were fractionated firstly by a stainless steel mesh and cell clusters having the size of 250–840 $\mu$m were obtained. A medium having a specific gravity of 1.07 (g/ml) was produced by the use of Ficoll and the above-mentioned cells were layered over it and centrifuged at 700 rpm for 6 minutes. The cells were fractionated into two layers according to the difference of the specific gravity. The cells contained in the layer of 1.07 g/ml or less were fractionated and washed with 2% sucrose solution three times or more, to wash off Ficoll. After the washing, 1 g (fresh weight) of the cells was inoculated to an Erlenmeyer flask containing 20 ml of liquid Woody Plant Medium and shake culture was carried out at 25° C. for 14 days. On the 14th day after starting the culture, methyl ester of jasmonic acid was added to it to give the final concentration of 250 $\mu$M, and the culture was further carried out for another 7 days. After completing the culture, the procedure of Example 15 was carried out. The results are shown in Table 9. The productivity of the taxane-type diterpenes could be greatly improved by the combination of the selection of cells having a particular specific gravity and the addition of the methyl ester of jasmonic acid.

Comparative Example 12

The procedure of Example 21 was carried out except that the methyl ester of jasmonic acid was not added. The results are shown in Table 9.

Example 22

250 $\mu$M of methyl ester of jasmonic acid was added to cultured cells of Taxus brevifolia NUTT obtained on the 14th day after starting the culture by the method of Example 15, and the culture was further carried out for another 7 days. After completing the culture, the procedure of Example 15 was carried out. The results are shown in Table 10.

Comparative Example 13

The procedure of Example 22 was carried out except that methyl ester of jasmonic acid was not added. The results are shown in Table 10.

Example 23

The procedure of Example 22 was carried out except that cultured cells of T. media were used. The results are shown in Table 10.

Comparative Example 14

The procedure of Example 23 was carried out except that the methyl ester of jasmonic acid was not added. The results are shown in Table 10.

TABLE 7

| | concentration of methyl jasmonate ($\mu$M) | cell yield (g/l) | yield *) of baccatin III (mg/l) | yield *) of taxol (mg/l) | yield *) of cephalomannine (mg/l) |
|---|---|---|---|---|---|
| Comparative Example 9 | 0 | 12.2 | 0.2 | 2.8 | 1.5 |
| Example 15 | 0.01 | 12.2 | 0.3 | 3.2 | 1.6 |
| Example 15 | 0.1 | 12.1 | 0.3 | 4.2 | 1.6 |
| Example 15 | 1 | 11.3 | 0.4 | 4.9 | 1.8 |
| Example 15 | 10 | 11.3 | 0.7 | 10.8 | 2.1 |
| Example 15 | 50 | 10.9 | 3.1 | 10.9 | 2.2 |
| Example 15 | 100 | 9.8 | 9.2 | 13.5 | 2.0 |
| Example 15 | 250 | 10.0 | 12.9 | 15.1 | 2.0 |
| Example 15 | 500 | 10.6 | 13.0 | 12.6 | 1.9 |
| Example 15 | 1000 | 5.9 | 1.2 | 3.1 | 1.8 |
| Example 16 | 100 (25 × 4) | 10.7 | 14.9 | 16.7 | 2.2 |
| Example 17 | 100 | 7.2 | 1.2 | 4.5 | 1.7 |
| Example 18 | 100 | 9.7 | 10.6 | 14.2 | 2.1 |

*) The yield was calculated based on the total amount of production (in the cell + in the medium).

TABLE 8

| | concentration of jasmonic acid ($\mu$M) | cell yield (g/l) | yield *) of baccatin III (mg/l) | yield *) of taxol (mg/l) | yield *) of cephalomannine (mg/l) |
|---|---|---|---|---|---|
| Comparative Example 10 | 0 | 12.2 | 0.2 | 1.2 | 0.4 |
| Example 19 | 0.01 | 12.2 | 0.3 | 2.2 | 0.6 |
| Example 19 | 0.1 | 12.2 | 0.3 | 3.4 | 0.6 |
| Example 19 | 1 | 11.6 | 0.3 | 5.9 | 0.8 |
| Example 19 | 10 | 11.5 | 0.5 | 8.3 | 2.6 |
| Example 19 | 50 | 11.4 | 2.5 | 10.2 | 2.2 |
| Example 19 | 100 | 10.3 | 7.2 | 12.8 | 3.0 |
| Example 19 | 250 | 10.1 | 10.6 | 14.7 | 2.7 |
| Example 19 | 500 | 10.2 | 12.0 | 11.1 | 1.1 |
| Example 19 | 1000 | 6.7 | 1.2 | 1.2 | 0.5 |

*) The yield was calculated based on the total amount of production (in the cell + in the medium).

TABLE 9

| | concentration of methyl jasmonate ($\mu$M) | cell yield (g/l) | yield *) of baccatin III (mg/l) | yield *) of taxol (mg/l) | yield *) of cephalomannine (mg/l) |
|---|---|---|---|---|---|
| Comparative Example 12 | 0 | 12.6 | 0.5 | 6.3 | 2.2 |
| Example 21 | 250 | 10.2 | 18.7 | 43.1 | 3.2 |

*) The yield was calculated based on the total amount of production (in the cell + in the medium).

TABLE 10

| | concentration of methyl jasmonate ($\mu$M) | cell yield (g/l) | yield *) of baccatin III (mg/l) | yield *) of taxol (mg/l) | yield *) of cephalomannine (mg/l) |
|---|---|---|---|---|---|
| Comparative Example 13 | 0 | 12.5 | 0.1 | 0.2 | 0.2 |
| Example 22 | 250 | 10.2 | 3.4 | 4.3 | 0.5 |
| Comparative Example 14 | 0 | 14.2 | 0.2 | 0.3 | 0.1 |
| Example 23 | 250 | 12.6 | 12.4 | 4.4 | 0.2 |

*) The yield was calculated based on the total amount of production (in the cell + in the medium).

Example 24

A part of stem of *Taxus baccata* LINN which had been previously sterilized with 2% antiformin solution or 70% ethanol solution and the like, was placed on solid Woody Plant Medium (containing gelan gum of 0.25by weight) to which naphthalenacetic acid had been added to give the concentration of $10^{-5}$M, and static culture was carried out at 25° C. in a dark place to provide callus of Taxus baccata LINN. One gram (fresh weight) of the callus was inoculated to an Erlenmeyer flask containing 20 ml of liquid Woody Plant Medium to which the above-mentioned component was added to give the same concentration and shake culture was carried out with a rotary shaker (amplification of 25 mm, 100 rpm) and the callus was subcultured in every 21 days to accelerate the growth rate thereof.

One gram (fresh weight) of the cultured cells thus obtained was inoculated to an Erlenmeyer flask containing 20 ml of liquid Woody Plant Medium to which the above-mentioned component was added to give the same concentration, and $[Ag(S_2O_3)_2]^{3-}$ was added to it as a compound containing a heavy metal to give the final concentration of $10^{-9}$M–1M. Then shake culture was carried out at 25° C. for 21 days.

After completing the culture, cultured cells of *Taxus baccata* LINN were harvested by filtration and lyophilized, then the dry weight was measured to obtain the growth rate thereof. Taxane-type diterpenes were extracted from the dried callus with methanol and the like, and they were determined by comparing with standard taxol, cephalomannine, and baccatin III using high performance liquid chromatography to measure the yields of the taxane-type diterpenes. The results are shown in Table 11.

Example 25

The procedure of Example 24 was carried out except that $[Ag(S_2O_3)_2]^{3-}$ was added on the 7th day after starting the culture to give the final concentration of $10^{-3}$M and the culture was further carried out for another 14 days. After the completion of the culture, the procedure of the Example 24 was carried out. The results are shown in Table 11.

Example 26

The procedure of Example 24 was carried out except that $[Ag(S_2O_3)_2]^{3-}$ was added on the 14th day after starting the culture to give the final concentration of $10^{-3}$M and the culture was further carried out for another 7 days. After the completion of the culture, the procedure of the Example 24 was carried out. The results are shown in Table 11.

Example 27

The procedure of Example 24 was carried out, except that $[Ag(S_2O_3)_2]^{3-}$ was added on the 18th day after starting the culture to give the final concentration of $10^{-3}$M and the culture was further carried out for another 3 days. After the completion of the culture, the procedure of Example 24 was carried out. The results are shown in Table 11.

Example 28

The procedure of Example 24 was carried out, except that $[Ag(S_2O_3)_2]^{3-}$ was added successively a total of 5 times at 4 days' intervals starting from the start (0 day) of the culture (to give the final concentration of $2\times10^{-4}$M each time, and to give the total concentration of $10^{-3}$M). The results are shown in Table 11.

Example 29

The procedure of Example 24 was carried out except that methyl ester of jasmonic acid (which is a compound represented by the general formula (III) wherein $R^{1a}$, $R^{1b}R^{1}c$, $R^{1d}$, $R^{1e}$, $R^{1f}$, $R^2$, $R^3$, $R^4$, $R^5$, and $R^6$ are hydrogen atoms, $R^7$ is methoxy group, n is 1 and $C^3$ and $C^4$ have a double bond between them) was added on the 14th day after starting the culture to give the final concentration of $10^{-4}$M. The results are shown in Table 11.

Example 30

The procedure of Example 24 was carried out except that the flask was put in a vessel (the capacity of 3000 ml) having a gas feed opening and a gas discharge opening, then the vessel was closed hermetically, and air was so mixed with nitrogen that the concentration of the oxygen in a gas to be supplied to the cells to be cultured became 10%, and the gas was supplied through the feed opening at the rate of 25 ml per minute. The results are shown in Table 11.

Example 31

The procedure of Example 30 was carried out except that methyl ester of jasmonic acid was added on the 14th day of the culture to give the final concentration of $10^{-4}$M. The results are shown in Table 11.

Example 32

The procedure of Example 24 was carried out except that silver nitrate $Ag(NO_3)$ of $10^{-3}$M was added at the start (0 day) of the culture instead of $[Ag(S_2O_3)_2]^{3-}$. The results are shown in Table 11.

Example 33

The procedure of Example 32 was carried out except that silver nitrate of $10^{-3}$M was added on the 14th day of the culture. The results are shown in Table 11.

Comparative Example 15

The procedure of Example 24 was carried out except that $[Ag(S_2O_3)_2]^{3-}$ was not added. The results are shown in Table 11.

Example 34

The procedure of Example 24 was carried out except that cobalt chloride ($CoCl_2$) was added instead of $[Ag(S_2O_3)_2]^{3-}$ as a compound containing the heavy metal to give the final concentration of $10^{-9}$M–1M. The results are shown in Table 12.

Example 35

The procedure of Example 34 was carried out except that cobalt chloride ($CoCl_2$) was added instead of $[Ag(S_2O_3)_2]^{3-}$ to give the final concentration of $10^{-5}$M on the 7th day after starting the culture and the culture was further carried out for another 14 days. After completing the culture, the procedure of Example 34 was carried out. The results are shown in Table 12.

Example 36

The procedure of Example 34 was carried out except that cobalt chloride was added to give the final concentration of $10^{-5}$ M on the 14th day after starting the culture and the culture was further carried out for another 7 days. After completing the culture, the process of Example 34 was carried out. The results are shown in Table 12.

Example 37

The procedure of Example 34 was carried out except that cobalt chloride was added to give the final concentration of $10^{-5}$M on the 18th day after starting the culture, and the culture was further carried out for another 3 days. After completing the culture, the procedure of Example 34 was carried out. The results are shown in Table 12.

Example 38

The procedure of Example 34 was carried out except that cobalt chloride was added successively a total of 5 times at 4 days' intervals starting from the start (0 day) of the culture (to give the final concentration of $2\times10^{-6}$M each time, and to give the total concentration of $10^{-5}$M). The results are shown in Table 12.

Example 39

The procedure of Example 34 was carried out except that methyl ester of jasmonic acid (which is a compound represented by the general formula (III) wherein $R^{1a}$, $R^{1b}$, $R^{1c}$, $R^{1d}$, $R^{1e}$, $R^{1f}$, $R^2$, $R^3$, $R^4$, $R^5$, and $R^6$ are hydrogen atoms, $R^7$ is methoxy group, n is 1 and $C^3$ and $C^4$ have a double bond between them) was added as one of jasmonic acids to give the final concentration of $10^{-4}$M on the 14th day after starting the culture. The results are shown in Table 12.

Example 40

The procedure of Example 34 was carried out except that the flask was put in a vessel (the capacity of 3000 ml) having a gas feed opening and a gas discharge opening, then the vessel was closed hermetically, and air was so mixed with nitrogen that the concentration of the oxygen in a gas to be supplied to the cells to be cultured became 10% and the gas was supplied through the feed opening at the rate of 25 ml per minute. The results are shown in Table 12.

Example 41

The procedure of Example 40 was carried out except that methyl ester of jasmonic acid was added to give the final concentration of $10^{-4}$M on the 14th day of the culture. The results are shown in Table 12.

Medium to which the above-mentioned component was added to give the same concentration and shake culture was

TABLE 11

| | concentration of silver thiosulfate (M) | concentration of silver nitrate (M) | concentration of methyl jasmonate (M) | max oxygen concentration in the gas phase (%) | growth rate (times) | yield[a] of baccatin III(mg/l) | yield[a] of cephalomannine (mg/l) | yield[1] of taxol (mg/l) | total yield[a] of taxane (mg/l) |
|---|---|---|---|---|---|---|---|---|---|
| Comparative Example 15 | 0 | 0 | 0 | 20 | 2.7 | 0.14 | 0.56 | 0.28 | 0.98 |
| Example 24 | $10^{-9}$ | 0 | 0 | 20 | 2.7 | 0.20 | 0.56 | 0.33 | 1.09 |
| " | $10^{-8}$ | 0 | 0 | 20 | 2.8 | 0.29 | 0.97 | 0.76 | 2.02 |
| " | $10^{-7}$ | 0 | 0 | 20 | 2.7 | 0.34 | 2.47 | 1.57 | 4.38 |
| " | $10^{-6}$ | 0 | 0 | 20 | 2.6 | 1.06 | 2.86 | 1.80 | 5.72 |
| " | $10^{-5}$ | 0 | 0 | 20 | 2.7 | 1.13 | 4.10 | 7.95 | 13.18 |
| " | $10^{-4}$ | 0 | 0 | 20 | 2.7 | 7.62 | 5.11 | 14.53 | 27.26 |
| " | $10^{-3}$ | 0 | 0 | 20 | 2.7 | 27.90 | 5.96 | 25.13 | 58.99 |
| " | $10^{-2}$ | 0 | 0 | 20 | 2.3 | 0.72 | 5.50 | 5.80 | 12.02 |
| " | $10^{-1}$ | 0 | 0 | 20 | 1.9 | 0.26 | 2.15 | 1.37 | 3.78 |
| " | 1 | 0 | 0 | 20 | 1.2 | 0.08 | 0.36 | 0.20 | 0.64 |
| Example 25 | $10^{-3}$ | 0 | 0 | 20 | 2.2 | 11.71 | 4.86 | 10.64 | 27.21 |
| Example 26 | $10^{-3}$ | 0 | 0 | 20 | 2.5 | 2.29 | 3.83 | 4.47 | 10.59 |
| Example 27 | $10^{-3}$ | 0 | 0 | 20 | 2.9 | 0.28 | 1.44 | 1.55 | 3.27 |
| Example 28 | $10^{-3}$ | 0 | 0 | 20 | 2.4 | 4.15 | 7.27 | 20.94 | 32.36 |
| Example 29 | $10^{-3}$ | 0 | $10^{-4}$ | 20 | 2.7 | 25.14 | 12.57 | 33.61 | 71.32 |
| Example 30 | $10^{-3}$ | 0 | 0 | 10 | 2.7 | 22.81 | 9.08 | 27.45 | 59.34 |
| Example 31 | $10^{-3}$ | 0 | $10^{-4}$ | 10 | 2.7 | 27.00 | 12.34 | 34.73 | 74.07 |
| Example 32 | 0 | $10^{-3}$ | 0 | 20 | 2.8 | 3.01 | 7.54 | 12.66 | 23.21 |
| Example 33 | 0 | $10^{-3}$ | 0 | 20 | 2.8 | 2.18 | 6.49 | 11.91 | 20.58 |

[a]: The yield was calculated based on the total amount of production (in the cell + in the medium)
[b]: The total yield was calculated by adding the yield of baccatin III, the yield of cephalomannine and the yield of taxol.

TABLE 12

| | concentration of cobalt chloride (M) | concentration of methyl jasmonate (M) | max oxygen concentration in the gas phase (%) | growth rate (times) | yield[a] of baccatin III (mg/l) | yield[a] of cephalomannine (mg/l) | yield[1] of taxol (mg/l) | total yield[b] of taxane (mg/l) |
|---|---|---|---|---|---|---|---|---|
| Comparative Example 15 | 0 | 0 | 20 | 2.7 | 0.14 | 0.56 | 0.28 | 0.98 |
| Example 34 | $10^{-9}$ | 0 | 20 | 2.5 | 0.15 | 0.56 | 0.27 | 0.98 |
| " | $10^{-8}$ | 0 | 20 | 2.6 | 0.15 | 0..61 | 0.29 | 1.05 |
| " | $10^{-7}$ | 0 | 20 | 2.6 | 0.16 | 0.63 | 0.29 | 1.08 |
| " | $10^{-6}$ | 0 | 20 | 2.4 | 2.25 | 5.79 | 8.32 | 16.36 |
| " | $10^{-5}$ | 0 | 20 | 3.2 | 5.68 | 6.50 | 16.11 | 28.29 |
| " | $10^{-4}$ | 0 | 20 | 2.7 | 1.64 | 3.46 | 4.92 | 10.02 |
| " | $10^{-3}$ | 0 | 20 | 2.2 | 1.57 | 2.03 | 4.38 | 7.98 |
| " | $10^{-2}$ | 0 | 20 | 1.4 | 0.44 | 0.78 | 0.92 | 2.14 |
| " | $10^{-1}$ | 0 | 20 | 0.8 | 0.11 | 0.42 | 0.55 | 1.08 |
| " | 1 | 0 | 20 | 0.6 | 0 | 0 | 0 | 0 |
| Example 35 | $10^{-5}$ | 0 | 20 | 3.2 | 4.36 | 5.98 | 10.22 | 20.56 |
| Example 36 | $10^{-5}$ | 0 | 20 | 3.1 | 2.01 | 4.37 | 7.10 | 13.48 |
| Example 37 | $10^{-5}$ | 0 | 20 | 2.9 | 1.17 | 1.11 | 1.32 | 3.60 |
| Example 38 | $10^{-5}$ | 0 | 20 | 2.6 | 5.32 | 6.58 | 15.76 | 27.66 |
| Example 39 | $10^{-5}$ | $10^{-4}$ | 20 | 2.5 | 23.00 | 9.46 | 30.32 | 62.78 |
| Example 40 | $10^{-5}$ | 0 | 10 | 2.7 | 17.61 | 7.99 | 26.64 | 52.24 |
| Example 41 | $10^{-5}$ | $10^{-4}$ | 10 | 2.4 | 25.85 | 15.21 | 33.77 | 74.83 |

[a]: The yield was calculated based on the total amount of production (in the cell + in the medium)
[b]: The total yield was calculated by adding the yield of baccatin III, the yield of cephalomannine and the yield of taxol.

Example 42

A part of stem of *Taxus baccata* LINN which had been previously sterilized with 2% antiformin solution or 70% ethanol solution and the like, was placed on solid Woody Plant Medium (containing gelan gum of 0.25% by weight) to which naphthalenacetic acid had been added to give the concentration of $10^{-5}$M, and static culture was carried out at 25° C. in a dark place to provide *Taxus baccata* LINN callus. One gram (fresh weight) of the callus was inoculated to an Erlenmeyer flask containing 20 ml of liquid Woody Plant Medium to which the above-mentioned component had been added to give the same concentration and shake culture was carried out with a rotary shaker (amplification of 25 mm, 100 rpm) and the callus was subcultured in every 21 days to accelerate the growth rate thereof.

One gram (fresh weight) of the cultured cells thus obtained was inoculated to an Erlenmeyer flask containing 20 ml of liquid Woody Plant Medium to which the above-mentioned component had been added to give the same concentration, then spermidine was added to it as amine to give the final concentration of $10^{-9}$M–1M. Then shake culture was carried out at 25° C. for 21 days.

After completing the culture, cultured cells of *Taxus baccata* LINN were harvested by filtration and lyophilized, then the dry weight was measured to obtain the growth rate thereof. Taxane-type diterpenes were extracted from the dried cells with methanol and the like, and they were determined by comparing with standard taxol, cephalomannine, and baccatin III using high performance liquid chromatography to measure the yields of the taxane-type diterpene. The results are shown in Table 13.

Example 43

The procedure of Example 42 was carried out except that spermidine was added to give the final concentration of $10^{-5}$M on the 7th day after starting the culture and the culture was further continued for another 14 days. After completing the culture, the procedure of Example 42 was carried out. The results are shown in Table 13.

Example 44

The procedure of Example 42 was carried out except that spermidine was added to give the final concentration of $10^{-5}$M on the 14th day after starting the culture and the culture was further continued for another 7 days. After completing the culture, the procedure of Example 42 was carried out. The results are shown in Table 13.

Example 45

The procedure of Example 42 was carried out except that spermidine was added to give the final concentration of $10^{-5}$M on the 18th day after starting the culture and the culture was further continued for another 3 days. After completing the culture, the procedure of Example 42 was carried out. The results are shown in Table 13.

Example 46

The procedure of Example 42 was carried out except that spermidine was added successively a total of 5 times at 4 day' intervals starting from the start (0 day) of the culture (to give the final concentration of $2 \times 10^{-6}$M each time, and to give the total concentration of $10^{-5}$M). The results are shown in Table 13.

Example 47

The procedure of Example 42 was carried out except that methyl ester of jasmonic acid (which is a compound represented by the general formula (III) wherein $R^{1a}$, $R^{1b}$, $R^{1c}$, $R^{1d}$, $R^{1e}$, $R^{1f}$, $R^2$, $R^3$, $R^4$, $R^5$, and $R^6$ are hydrogen atoms, $R^7$ is methoxy group, n is 1 and $C^3$ and $C^4$ have a double bond between them) was added as one of jasmonic acids on the 14th day after starting the culture to give the final concentration of $10^{-4}$M. The results are shown in Table 13.

Example 48

The procedure of Example 42 was carried out except that the flask was placed in a chamber (the capacity of 3000 ml) having a gas feed opening and a gas discharge opening, then the chamber was closed hermetically, and air was so mixed with nitrogen that the concentration of the oxygen in a gas to be supplied to the cells to be cultured became 10% and the gas was supplied through the feed opening at the rate of 25 ml per minute. The results are shown in Table 13.

Example 49

The procedure of Example 48 was carried out except that methyl ester of jasmonic acid was added to give the final concentration of $10^{-4}$M on the 14th day of the culture. The results are shown in Table 13.

Comparative Example 16

The procedure of Example 42 was carried out except that spermidine was not added. The results are shown in Tables 13–15.

Example 50

The procedure of Example 42 was carried out except that spermin was added instead of spermidine to give the final concentration of $10^{-9}$M–1M. The results are shown in Table 14.

Example 51

The procedure of Example 42 was carried out except that putrescine was added instead of spermin to give the final concentration of $10^{-9}$M–1M. The results are shown in Table 15.

TABLE 13

| | concentration of spermidine (M) | concentration of methyl jasmonate (M) | max oxygen concentration in the gas phase (%) | growth rate (times) | yield[a] of baccatin III (mg/l) | yield[a] of cephalo-mannine (mg/l) | yield[1] of taxol (mg/l) | total yield[b] of taxane (mg/l) |
|---|---|---|---|---|---|---|---|---|
| Comparative Example 16 | 0 | 0 | 20 | 2.7 | 0.14 | 0.56 | 0.28 | 0.98 |
| Example 42 | $10^{-9}$ | 0 | 20 | 2.9 | 0.31 | 0.58 | 0.32 | 1.21 |
| " | $10^{-8}$ | 0 | 20 | 3.1 | 0.66 | 1.74 | 1.99 | 4.39 |
| " | $10^{-7}$ | 0 | 20 | 3.1 | 1.34 | 5.79 | 11.76 | 18.89 |
| " | $10^{-6}$ | 0 | 20 | 3.2 | 3.61 | 6.04 | 13.51 | 23.16 |
| " | $10^{-5}$ | 0 | 20 | 3.1 | 6.59 | 7.30 | 19.28 | 33.17 |
| " | $10^{-4}$ | 0 | 20 | 3.1 | 2.78 | 6.49 | 12.96 | 22.23 |
| " | $10^{-3}$ | 0 | 20 | 2.9 | 2.63 | 4.59 | 10.09 | 17.31 |
| " | $10^{-2}$ | 0 | 20 | 2.0 | 0.82 | 2.42 | 3.89 | 7.13 |
| " | $10^{-1}$ | 0 | 20 | 2.1 | 0.41 | 1.00 | 1.94 | 3.35 |
| " | 1 | 0 | 20 | 1.4 | 0.10 | 0.03 | 0.08 | 0.21 |
| Example 43 | $10^{-5}$ | 0 | 20 | 2.9 | 6.08 | 6.13 | 15.24 | 27.45 |
| Example 44 | $10^{-5}$ | 0 | 20 | 2.9 | 5.46 | 5.32 | 10.20 | 20.98 |
| Example 45 | $10^{-5}$ | 0 | 20 | 3.0 | 2.95 | 2.90 | 5.63 | 11.48 |
| Example 46 | $10^{-5}$ | 0 | 20 | 2.9 | 6.30 | 6.01 | 15.43 | 27.74 |
| Example 47 | $10^{-5}$ | $10^{-4}$ | 20 | 2.6 | 18.96 | 9.74 | 21.55 | 50.25 |

TABLE 13-continued

| | concentration of spermidine (M) | concentration of methyl jasmonate (M) | max oxygen concentration in the gas phase (%) | growth rate (times) | yield[a] of baccatin III (mg/l) | yield[a] of cephalo-mannine (mg/l) | yield[1] of taxol (mg/l) | total yield[b] of taxane (mg/l) |
|---|---|---|---|---|---|---|---|---|
| Example 48 | $10^{-5}$ | 0 | 10 | 2.7 | 13.43 | 7.81 | 19.05 | 40.29 |
| Example 49 | $10^{-5}$ | $10^{-4}$ | 10 | 2.6 | 19.65 | 8.57 | 29.67 | 57.89 |

[a]: The yield was calculated based on the total amount of production (in the cell + in the medium)
[b]: The total yield was calculated by adding the yield of baccatin III, the yield of cephalomannine and the yield of taxol.

TABLE 14

| | concentration of spermin (M) | growth rate (times) | yield[a] of baccatin III (mg/l) | yield[a] of cephalo-mannine (mg/l) | yield[a] of taxol (mg/l) | total yield[b] of taxane (mg/l) |
|---|---|---|---|---|---|---|
| Comparative Example 16 | 0 | 2.7 | 0.14 | 0.56 | 0.28 | 0.98 |
| Example 50 | $10^{-9}$ | 2.9 | 0.50 | 0.64 | 0.72 | 1.86 |
| " | $10^{-8}$ | 2.3 | 0.62 | 1.01 | 1.79 | 3.42 |
| " | $10^{-7}$ | 2.4 | 0.68 | 1.32 | 2.17 | 4.17 |
| " | $10^{-6}$ | 2.4 | 0.89 | 1.97 | 4.03 | 6.89 |
| " | $10^{-5}$ | 2.1 | 2.09 | 5.63 | 9.46 | 17.18 |
| " | $10^{-4}$ | 2.3 | 1.64 | 4.09 | 6.23 | 11.96 |
| " | $10^{-3}$ | 2.0 | 0.76 | 2.68 | 4.78 | 8.22 |
| " | $10^{-2}$ | 2.1 | 0.70 | 1.54 | 1.06 | 3.30 |
| " | $10^{-1}$ | 1.4 | 0.39 | 0.32 | 0.58 | 1.29 |
| " | 1 | 1.0 | 0.10 | 0.04 | 0.08 | 0.22 |

[a]: The yield was calculated based on the total amount of production (in the cell + in the medium).
[b]: The total yield was calculated by adding the yield of baccatin III, the yield of cephalomannine and the yield of taxol.

TABLE 15

| | concentration of putrescine (M) | growth rate (times) | yield[a] of baccatin III (mg/l) | yield[a] of cephalo-mannine (mg/l) | yield[a] of taxol (mg/l) | total yield[b] of taxane (mg/l) |
|---|---|---|---|---|---|---|
| Comparative Example 16 | 0 | 2.7 | 0.14 | 0.56 | 0.28 | 0.98 |
| Example 51 | $10^{-9}$ | 2.8 | 0.36 | 0.70 | 0.69 | 1.75 |
| " | $10^{-8}$ | 2.8 | 0.40 | 1.02 | 1.52 | 2.94 |
| " | $10^{-7}$ | 2.7 | 1.10 | 2.31 | 3.47 | 6.88 |
| " | $10^{-6}$ | 3.0 | 5.74 | 5.51 | 8.19 | 19.44 |
| " | $10^{-5}$ | 3.1 | 6.98 | 5.37 | 11.44 | 23.79 |
| " | $10^{-4}$ | 2.6 | 6.60 | 5.25 | 10.80 | 22.65 |
| " | $10^{-3}$ | 2.2 | 1.95 | 1.88 | 3.07 | 6.90 |
| " | $10^{-2}$ | 1.8 | 1.13 | 0.99 | 1.06 | 3.18 |
| " | $10^{-1}$ | 1.1 | 0.80 | 0.97 | 0.97 | 2.74 |
| " | 1 | 1.0 | 0.01 | 0.22 | 0.13 | 0.36 |

[a]: The yield was calculated based on the total amount of production (in the cell + in the medium).
[b]: The total yield was calculated by adding the yield of baccatin III, the yield of cephalomannine and the yield of taxol.

Example 52

A part of stem of *Taxus baccata* LINN which had been previously sterilized with 2% antiformin solution or 70% ethanol solution and the like, was placed on solid Woody Plant Medium (containing gelan gum of 0.25% by weight) to which naphthalenacetic acid had been added to give the concentration of $10^{-5}$M, and static culture was carried out at 25° C. in a dark place to provide *Taxus baccata* LINN callus. One gram (fresh weight) of the callus was inoculated to an Erlenmeyer flask containing 20 ml of liquid Woody Plant Medium to which the above-mentioned component had been added to give the same concentration and shake culture was carried out with a rotary shaker (amplification of 25 mm, 100 rpm) and the callus was subcultured in every 21 days to accelerate the growth rate thereof.

One gram (fresh weight) of the cultured cells thus obtained was inoculated to an Erlenmeyer flask containing 20 ml of liquid Woody Plant Medium to which the above-mentioned component had been added to give the same concentration, and shake culture was carried out at 25° C. for 14 days. Acetylsalicylic acid ($HOOCC_6H_4OCOCH_3$) was added as antiethylene agent on the 14th day after starting the culture to give the final concentration of $10^{-9}$M–1M and the culture was further continued for another 7 days.

After completing the culture, cultured cells of *Taxus baccata* LINN were harvested by filtration and lyophilized, then the dry weight was measured to obtain the growth rate thereof. Taxane-type diterpenes were extracted from the dried cells with methanol and the like, and they were determined by comparing with standard taxol, cephalomannine, and baccatin III using high performance liquid chromatography to measure the yields of the taxane-type diterpenes. The results are shown in Table 16.

Example 53

The procedure of Example 52 was carried out except that acetylsalicylic acid was added at the start (0 day) of the culture to give the final concentration of $10^{-5}$M and the culture was carried out for another 21 days. After completing the culture, the procedure of Example 52 was carried out. The results are shown in Table 16.

Example 54

The procedure of Example 52 was carried out except that acetylsalicylic acid was added on the 7th day after starting the culture to give the final concentration of $10^{-5}$M and the culture was further continued for another 14 days. After completing the culture, the procedure of the Example 52 was carried out. The results are shown in Table 16.

Example 55

The procedure of Example 52 was carried out except that acetylsalicylic acid was added on the 18th day after starting the culture to give the final concentration of $10^{-5}$M and the culture was further continued for another 3 days. After completing the culture, the procedure of the Example 52 was carried out. The results are shown in Table 16.

Example 56

The procedure of Example 52 was carried out except that acetylsalicylic acid was added successively a total of 5 times at 2 days' intervals starting from the 7th day after starting the culture (to give the final concentration of $2 \times 10^{-6}$M each time, and to give the total concentration of $10^{-5}$M). The results are shown in Table 16.

Example 57

The procedure of Example 52 was carried out except that methyl ester of jasmonic acid (which is a compound represented by the general formula (III) wherein $R^{1a}$, $R^{1b}$, $R^{1c}$, $R^{1d}$, $R^{1e}$, $R^{1f}$, $R^2$, $R^3$, $R^4$, $R^5$, and R6 are hydrogen atoms, $R^7$ is methoxy group, n is 1 and $C^3$ and $C^4$ have a double bond between them) was added on the 14th day after starting the culture to give the final concentration of $10^{-4}$M. The results are shown in Table 16.

Example 58

The procedure of Example 52 was carried out, except that the flask was placed in a chamber (the capacity of 3000 ml) having a gas feed opening and a gas discharge opening, then the chamber was closed hermetically, and air was so mixed with nitrogen that the concentration of the oxygen in a gas to be supplied to the cells to be cultured became 10%, and the gas was supplied through the feed opening at the rate of 25 ml per minute. The results are shown in Table 16.

Example 59

The procedure of Example 58 was carried out except that methyl ester of jasmonic acid was added on the 14th day of the culture to give the final concentration of $10^{-4}$M. The results are shown in Table 16.

Reference Example 2

The procedure of Example 52 was carried out except that Ethrel of $10^{-3}$M was added instead of acetylsalicylic acid at the 14th day after starting the culture. The results are shown in Table 16.

Example 60

The procedure of Example 52 was carried out except that aminoxyacetic acid hydrochloride [($H_2NOCH_2COOH)_2 \cdot HCl$] was added as an antiethylene agent to give the final concentration of $10^{-9}$M–1M. The results are shown in Table 17.

Example 61

The procedure of Example 52 was carried out except that propyl gallate [$(HO)_3C_6H_2COOCH_2CH_2CH_3$] was added as an antiethylene agent to give the final concentration of $10^{-9}$M–1M. The results are shown in Table 18.

TABLE 16

| | concentration of acetylsalicylic acid (M) | concentration of methyl jasmonate (M) | max oxygen concentration in the gas phase (%) | ethylene concentration (M) | growth rate (times) | yield[a] of baccatin III(mg/l) | yield[a] of cephalomannine (mg/l) | yield[a] of taxol (mg/l) | total yield[b] of taxane (mg/l) |
|---|---|---|---|---|---|---|---|---|---|
| Comparative Example 17 | 0 | 0 | 20 | 0 | 2.7 | 0.14 | 0.56 | 0.28 | 0.98 |
| Example 52 | $10^{-9}$ | 0 | 20 | 0 | 2.7 | 0.25 | 0.62 | 0.48 | 1.35 |
| " | $10^{-8}$ | 0 | 20 | 20 | 2.8 | 0.79 | 0.64 | 0.89 | 2.32 |
| " | $10^{-7}$ | 0 | 20 | 0 | 2.9 | 0.79 | 1.27 | 0.90 | 2.96 |
| " | $10^{-6}$ | 0 | 20 | 0 | 2.5 | 0.83 | 2.73 | 3.00 | 6.56 |
| " | $10^{-5}$ | 0 | 20 | 0 | 2.7 | 1.52 | 6.96 | 13.42 | 21.90 |
| " | $10^{-4}$ | 0 | 20 | 0 | 2.7 | 1.48 | 6.54 | 11.15 | 19.17 |
| " | $10^{-3}$ | 0 | 20 | 0 | 2.6 | 1.06 | 3.30 | 4.44 | 8.80 |
| " | $10^{-2}$ | 0 | 20 | 0 | 2.6 | 1.01 | 0.70 | 1.61 | 3.32 |
| " | $10^{-1}$ | 0 | 20 | 0 | 2.0 | 0.58 | 0.12 | 0.70 | 1.40 |
| " | 1 | 0 | 20 | 0 | 1.5 | 0.01 | 0 | 0.01 | 0.02 |
| Example 53 | $10^{-5}$ | 0 | 20 | 0 | 2.6 | 0.42 | 1.76 | 2.98 | 5.16 |
| Example 54 | $10^{-5}$ | 0 | 20 | 0 | 2.7 | 0.91 | 3.55 | 4.22 | 8.68 |
| Example 55 | $10^{-5}$ | 0 | 20 | 0 | 2.7 | 1.22 | 6.39 | 9.58 | 17.19 |
| Example 56 | $10^{-5}$ | 0 | 20 | 0 | 2.6 | 1.09 | 5.46 | 10.02 | 16.57 |
| Example 57 | $10^{-5}$ | $10^{-4}$ | 20 | 0 | 2.4 | 11.52 | 6.60 | 15.11 | 33.23 |
| Example 58 | $10^{-5}$ | 0 | 10 | 0 | 2.4 | 7.28 | 6.46 | 11.80 | 25.54 |
| Example 59 | $10^{-5}$ | $10^{-4}$ | 10 | 0 | 2.3 | 14.79 | 6.69 | 18.91 | 40.39 |
| Reference Example 1 | 0 | 0 | 20 | $10^{-3}$ | 2.7 | 0.12 | 0.14 | 0.14 | 0.40 |
| Reference Example 2 | 0 | 0 | 20 | $10^{-3}$ | 2.7 | 0.05 | 0.16 | 0.09 | 0.30 |

[a]: The yield was calculated based on the total amount of production (in the cell + in the medium)
[b]: The total yield was calculated by adding the yield of baccatin III, the yield of cephalomannine and the yield of taxol.

Comparative Example 17

The procedure of Example 52 was carried out except that acetylsalicylic acid was not added. The results are shown in Tables 16.

Reference Example 1

The procedure of Example 52 was carried out except that Ethrel ($C_2H_6O_3ClP$) of $10^{-3}$M was added instead of acetylsalicylic acid, as an ethylene generating agent at the start (0 day) of the culture. The results are shown in Table 16.

TABLE 17

| | concentration of aminooxyacetic acid (M) | growth rate (times) | yield[a] of baccatin III (mg/l) | yield[a] of cephalomannine (mg/l) | yield[a] of taxol (mg/l) | total yield[b] of taxane (mg/l) |
|---|---|---|---|---|---|---|
| Comparative Example 17 | 0 | 2.7 | 0.14 | 0.56 | 0.28 | 0.98 |

TABLE 17-continued

| | concentration of aminooxyacetic acid (M) | growth rate (times) | yield[a] of baccatin III (mg/l) | yield[a] of cephalomannine (mg/l) | yield[a] of taxol (mg/l) | total yield[b] of taxane (mg/l) |
|---|---|---|---|---|---|---|
| Example 60 | $10^{-9}$ | 2.3 | 0.21 | 0.58 | 0.59 | 1.38 |
| " | $10^{-8}$ | 1.8 | 0.61 | 0.62 | 0.77 | 2.00 |
| " | $10^{-7}$ | 1.7 | 0.66 | 0.65 | 1.02 | 2.33 |
| " | $10^{-6}$ | 1.5 | 1.08 | 0.73 | 1.19 | 3.00 |
| " | $10^{-5}$ | 1.7 | 1.30 | 1.16 | 1.35 | 3.81 |
| " | $10^{-4}$ | 1.7 | 1.92 | 1.22 | 2.66 | 5.80 |
| " | $10^{-3}$ | 1.5 | 1.11 | 0.71 | 1.61 | 3.43 |
| " | $10^{-2}$ | 1.5 | 0.32 | 0.71 | 0.90 | 1.93 |
| " | $10^{-1}$ | 1.2 | 0.33 | 0.26 | 0.44 | 1.03 |
| " | 1 | 0.9 | 0 | 0 | 0 | 0 |

[a]: The yield was calculated based on the total amount of production (in the cell + in the medium).
[b]: The total yield was calculated by adding the yield of baccatin III, the yield of cephalomannine and the yield of taxol.

TABLE 18

| | concentration of propyl gallate (M) | growth rate (times) | yield[a] of baccatin III (mg/l) | yield[a] of cephalomannine (mg/l) | yield[a] of taxol (mg/l) | total yield[b] of taxane (mg/l) |
|---|---|---|---|---|---|---|
| Comparative Example 17 | 0 | 2.7 | 0.14 | 0.56 | 0.28 | 0.98 |
| Example 61 | $10^{-9}$ | 2.7 | 0.41 | 0.59 | 0.37 | 1.37 |
| " | $10^{-8}$ | 2.7 | 0.42 | 0.68 | 0.74 | 1.74 |
| " | $10^{-7}$ | 2.7 | 0.55 | 0.72 | 1.52 | 2.79 |
| " | $10^{-6}$ | 3.1 | 1.91 | 4.38 | 7.66 | 13.95 |
| " | $10^{-5}$ | 3.0 | 2.82 | 5.07 | 8.24 | 16.13 |
| " | $10^{-4}$ | 3.0 | 0.87 | 4.42 | 6.98 | 12.27 |
| " | $10^{-3}$ | 3.2 | 0.84 | 4.30 | 6.96 | 12.10 |
| " | $10^{-2}$ | 2.9 | 0.69 | 2.01 | 4.33 | 7.03 |
| " | $10^{-1}$ | 1.9 | 0.48 | 0.25 | 0.65 | 1.38 |
| " | 1 | 1.1 | 0.01 | 0 | 0 | 0.01 |

[a]: The yield was calculated based on the total amount of production (in the cell + in the medium).
[b]: The total yield was calculated by adding the yield of baccatin III, the yield of cephalomannine and the yield of taxol.

Example 62

A part of stem of *Taxus baccata* LINN which had been previously sterilized with 2% antiformin solution or 70% ethanol solution and the like, was placed on solid Woody Plant Medium (containing gelan gum of 0.25% by weight) to which naphthalenacetic acid had been added to give the concentration of $10^{-5}$M, and static culture was carried out at 25° C. in a dark place to provide *Taxus baccata* LINN callus. One gram (fresh weight) of the callus was inoculated to an Erlenmeyer flask containing 20 ml of liquid Woody Plant Medium to which the above-mentioned component had been added to give the same concentration and shake culture was carried out with a rotary shaker (amplification of 25 mm, 100 rpm) and the callus was subcultured in every 21 days to accelerate the growth rate of the callus.

One gram (fresh weight) of the cultured cells thus obtained was inoculated to an Erlenmeyer flask containing 20 ml of liquid Woody Plant Medium to which the above-mentioned component had been added to give the same concentration, and the flask was placed in a chamber (the capacity of 3000 ml) having a gas feed opening and a gas discharge opening, then the chamber was closed hermetically, and air was so mixed with nitrogen that the concentration of the oxygen in a gas to be supplied to the cells to be cultured became 4–15%, and while the gas was supplied through the feed opening at the rate of 25 ml per minute, shake culture was carried out at 25° C. for 21 days.

After completing the culture, cultured cells of *Taxus baccata* LINN were harvested by filtration and lyophilized, then the dry weight was measured to obtain the growth rate thereof. Taxane-type diterpenes were extracted from the dried cells with methanol and the like, and they were determined by comparing with standard taxol, cephalomannine, and baccatin III using high performance liquid chromatography to measure the yields of the taxane-type diterpenes. The results are shown in Table 19.

Comparative Example 18

The procedure of Example 62 was carried out except that the concentration of the oxygen in a gas to be supplied to the cells to be cultured was controlled to be 20%. The results are shown in Table 19.

Reference Example 3

The procedure of Example 62 was carried out except that the cultured cells inoculated to the flask were cultured in the atmosphere. The results are shown in Table 19.

Example 63

The procedure of Example 62 was carried out except that the concentration of the oxygen in a gas to be supplied to the cells to be cultured was controlled to be 10% and the mixed gas was supplied from the start of the culture for 3 days, then air was supplied till the end of the culture (for 18 days). The results are shown in Table 19.

Example 64

The procedure of Example 62 was carried out except that the concentration of the oxygen in a gas to be supplied to the cells to be cultured was controlled to be 10% and the mixed gas was supplied from the start of the culture for 7 days, then air was supplied till the end of the culture (for 14 days). The results are shown in Table 19.

Example 65

The procedure of Example 62 was carried out except that the concentration of the oxygen in a gas to be supplied to the cells to be cultured was controlled to be 10%, and the mixed gas was supplied from the start of the culture for 14 days, then air was supplied till the end of the culture (for 7 days). The results are shown in Table 19.

Example 66

The procedure of Example 62 was carried out except that methyl ester of jasmonic acid (which is a compound represented by the general formula (III) wherein $R^{1a}$, $R^{1b}$, $R^{1c}$, $R^{1d}$, $R^{1e}$, $R^{1f}$, $R^2$, R3, $R^4$, $R^5$, and $R^6$ are hydrogen atoms, $R^7$ is methoxy group, n is 1 and $C^3$ and $C^4$ have a double bond between them; 90% of which is in the trans-form, and 10% of which is in the cis-form) was added as one of jasmonic acids on the 14th day after starting the culture to give the final concentration of 10–1000 μM. The results are shown in Table 20. The productivity of taxane-type diterpene could be remarkably improved by combination of supply of oxygen of low concentration and addition of the methyl ester of jasmonic acid.

Example 67

Figure 3:
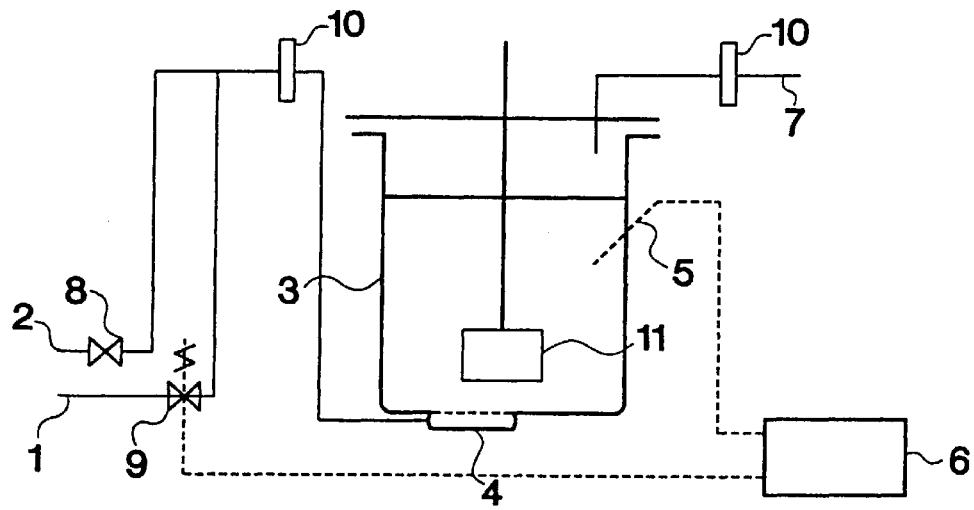
FIG. 3 is a diagram illustrating an example of a culture apparatus used for carrying out the tissue culture according to the second invention of the present application. Each numeral used in the FIG. 3 has the following meaning.

Eighty-five gram (fresh weight) of cultured cells obtained in Example 62 with accelerated growth rate were inoculated in a tank for stirred tank culture (capacity of 3000 ml) having an electrode for a dissolved oxygen concentration and a dissolved oxygen concentration controller, into which 1700 ml of liquid Woody Plant Medium had been poured. Then stirred tank culture was carried out at 25° C. for 21 days while the dissolved oxygen concentration in the medium was controlled to be 0.1 ppm or less by adjusting the mixing ratio of air and nitrogen. The schematic diagram of the culture apparatus is shown in FIG. 3 and the results are shown in Table 21.

Example 68

The procedure of Example 67 was carried out except that the concentration of the dissolved oxygen was controlled to be 1 ppm or less by adjusting the mixing ratio. The results are shown in Table 21.

Example 69

The procedure of Example 67 was carried out except that the concentration of the dissolved oxygen was controlled to be 2 ppm or less by adjusting the mixing ratio. The results are shown in Table 21.

Example 70

The procedure of Example 67 was carried out except that the concentration of the dissolved oxygen was controlled to be 4 ppm or less by adjusting the mixing ratio. The results are shown in Table 21.

Example 71

The procedure of Example 67 was carried out except that the concentration of the dissolved oxygen was controlled to be 6 ppm or less by adjusting the mixing ratio. The results are shown in Table 21.

Comparative Example 19

The procedure of Example 67 was carried out except that air was supplied. The results are shown in Table 21.

Example 72

The procedure of Example 67 was carried out except that the concentration of the dissolved oxygen in the medium was controlled to be 4 ppm or less from the start of the culture for 3 days by adjusting the mixing ratio, and air was supplied till the end of the culture (for 18 days). The results are shown in Table 21.

Example 73

The procedure of Example 67 was carried out except that the concentration of the dissolved oxygen in the medium was controlled to be 4 ppm or less from the start of the culture for 7 days by adjusting the mixing ratio, and air was supplied till the end of the culture (for 14 days). The results are shown in Table 21.

Example 74

The procedure of Example 67 was carried out, except that the concentration of the dissolved oxygen in the medium was controlled to be 4 ppm or less from the start of the culture for 14 days by adjusting the mixing ratio, and air was supplied till the end of the culture (for 7 days). The results are shown in Table 21.

TABLE 19

|  | max oxygen concentration in the gas phase (%) | growth rate (times) | yield[a] of baccatin III (mg/l) | yield[a] of cephalomannine (mg/l) | yield[a] of taxol (mg/l) | total yield[b] of taxane (mg/l) |
|---|---|---|---|---|---|---|
| Comparative Example 18 | 20 | 3.01 | 0.78 | 1.71 | 1.46 | 3.95 |
| Example 62 | 4 | 2.09 | 1.65 | 5.24 | 1.78 | 8.67 |
| " | 7 | 2.60 | 3.37 | 7.25 | 2.49 | 13.11 |
| " | 10 | 2.90 | 3.19 | 7.51 | 2.96 | 13.66 |
| " | 15 | 2.82 | 3.18 | 6.86 | 2.18 | 12.22 |
| Example 63 | 10[c] | 2.79 | 1.33 | 4.88 | 1.74 | 7.95 |
| Example 64 | 10[c] | 2.62 | 3.21 | 7.16 | 1.75 | 12.12 |
| Example 65 | 10[c] | 2.66 | 3.17 | 7.16 | 1.92 | 12.25 |
| Reference Example 3 | 20 | 3.03 | 0.77 | 1.23 | 0.95 | 2.95 |

[a]: The yield was calculated based on the total amount of production (in the cell + in the medium)
[b]: The total yield was calculated by adding the yield of baccatin III, the yield of cephalomannine and the yield of taxol.
[c]: The value shows the max oxygen concentration in the gas phase in the chamber during the mixed gas supply period.

TABLE 20

|  | max oxygen concentration in gas phase (%) | concentration of methyl jasmonate ($\mu$M) | growth rate (times) | yield[a] of baccatin III (mg/l) | yield[a] of taxol (mg/l) | yield[a] of cephalomannine (mg/l) | total yield[b] of taxane (mg/l) |
|---|---|---|---|---|---|---|---|
| Comparative Example 18 | 20 | 0 | 3.01 | 0.78 | 1.71 | 1.46 | 3.95 |
| Example 62 | 10 | 0 | 2.90 | 3.19 | 7.51 | 2.96 | 13.66 |
| Example 66 | 10 | 10 | 2.82 | 2.26 | 10.24 | 1.73 | 14.73 |
| " | 10 | 100 | 2.45 | 11.32 | 22.44 | 2.29 | 36.05 |
| " | 10 | 1000 | 1.47 | 2.10 | 5.04 | 1.47 | 8.61 |

[a]: The yield was calculated based an the total amount of production (in the cell + in the medium)
[b]: The total yield was calculated by adding the yield of baccatin III, the yield of cephalomannine and the yield of taxol.

TABLE 21

|  | max dissolved oxygen concentration in the medium (ppm) | growth rate (times) | yield[a] of baccatin III (mg/l) | yield[a] of taxol (mg/l) | yield[a] of cephalo- mannine (mg/l) | total yield[b] of taxane (mg/l) |
|---|---|---|---|---|---|---|
| Comparative Example 19 | 8 (100[c]) | 3.01 | 0.58 | 1.74 | 0.91 | 3.23 |
| Example 67 | 0.1 (1.25[c]) | 2.20 | 0.70 | 2.05 | 1.12 | 3.87 |
| Example 68 | 1 (12.5[c]) | 2.25 | 1.05 | 3.69 | 1.22 | 5.96 |
| Example 69 | 2 (25[c]) | 2.49 | 2.44 | 5.54 | 2.70 | 10.68 |
| Example 70 | 4 (50[c]) | 2.75 | 3.91 | 8.14 | 1.80 | 13.85 |
| Example 71 | 6 (75[c]) | 2.98 | 2.52 | 5.69 | 1.23 | 9.44 |
| Example 72 | 4[d] (50[e]) | 2.89 | 1.62 | 4.02 | 1.54 | 7.18 |
| Example 73 | 4[d] (50[e]) | 2.62 | 3.32 | 8.46 | 3.08 | 14.86 |
| Example 74 | 4[d] (50[e]) | 2.75 | 3.19 | 7.72 | 2.65 | 13.56 |

[a]: The yield was calculated based on the total amount of production (in the cell + in the medium)
[b]: The total yield was calculated by adding the yield of baccatin III, the yield of cephalomannine and the yield of taxol.
[c]: The figure in the parentheses shows the ratio (in %) of the max dissolved oxygen concentration in the comparative example and in each example with respect to the saturated dissolved oxygen concentration (8 ppm) at 25° C.
[d]: The value shows the max dissolved oxygen concentration in the culture medium during the mixed gas supply period.
[e]: The figure in the parentheses shows the ratio (in %) of the max dissolved oxygen concentration during the mixed gas supply period in each example with respect to the saturated dissolved oxygen concentration (8 ppm) at 25° C.

Example 75

A part of stem of *Taxus baccata* LINN which had been previously sterilized with 2% antiformin solution or 70% ethanol solution and the like, was placed on solid Woody Plant Medium (containing gelan gum of 0.25% by weight) to which naphthalenacetic acid had been added to give the concentration of $10^{-5}$M, and static culture was carried out at 25° C. in a dark place to provide Taxus baccata LINN callus. One gram (fresh weight) of the callus was inoculated to an Erlenmeyer flask containing 20 ml of liquid Woody Plant Medium to which the above-mentioned component had been added to give the same concentration and shake culture was carried out with a rotary shaker (amplification of 25 mm, 100 rpm), and the callus was subcultured in every 21 days to accelerate the growth rate thereof.

One gram (fresh weight) of the cultured cells thus obtained was fractionated firstly by a stainless steel mesh and cell clusters having the size of 250–840 μm were obtained. A density gradient with specific gravities of 1.03, 1.05, 1.07, 1.09 and 1.11 (g/ml) was produced by the use of Ficoll and the above-mentioned cells were layered over it and centrifuged at 700 rpm for 6 minutes. The cells were fractionated into each layer according to the difference of the specific gravity. The cells contained in each layer were so fractionated that they were not mixed each other and washed with 2% sucrose solution three times or more, to wash off Ficoll. After the washing, about 0.1 g (fresh weight) of the cells were transferred to a culture well having an inner diameter of 18 mm, containing 0.8 ml of liquid Woody Plant Medium and shake culture was carried out at 25° C. for 21 days. After culturing them for 21 days, the whole amount of the cells was transferred to a culture well having an inner diameter of 36 mm containing 3 ml of the above-mentioned liquid medium and shake culture was further continued at 25° C. for another 28 days.

Figure 4:
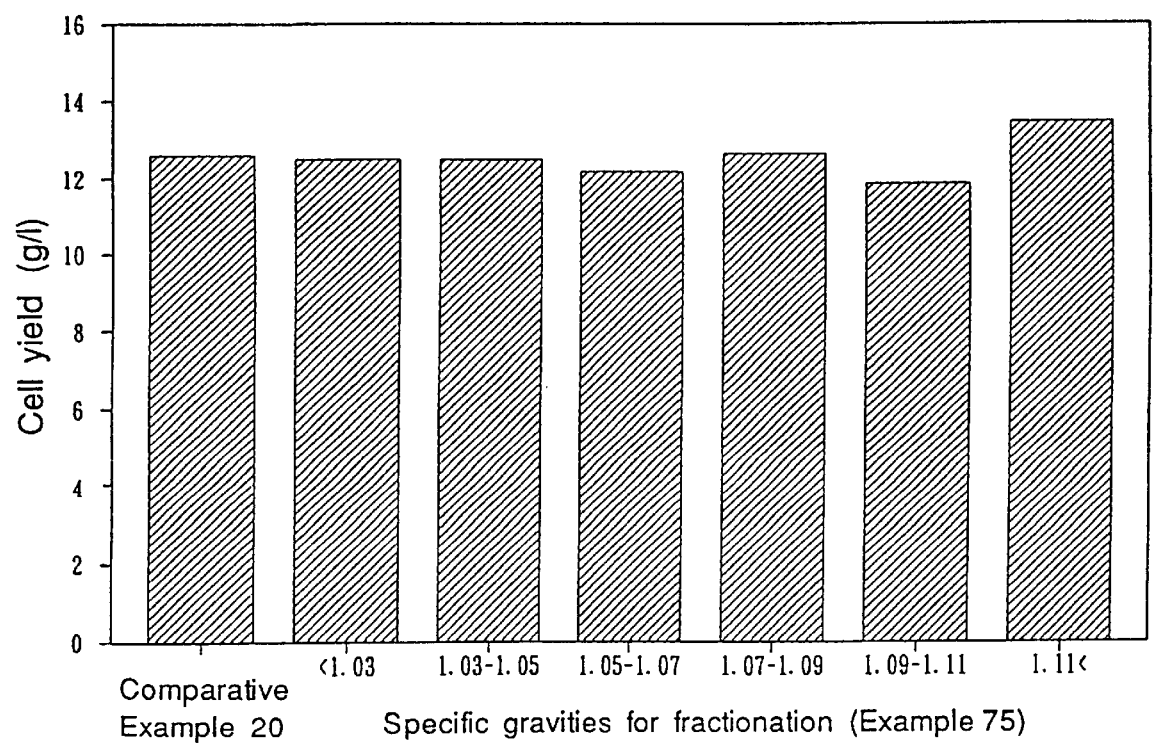
FIG. 4 is a graph showing the growth in the culture after the fractionation.
Figure 5:
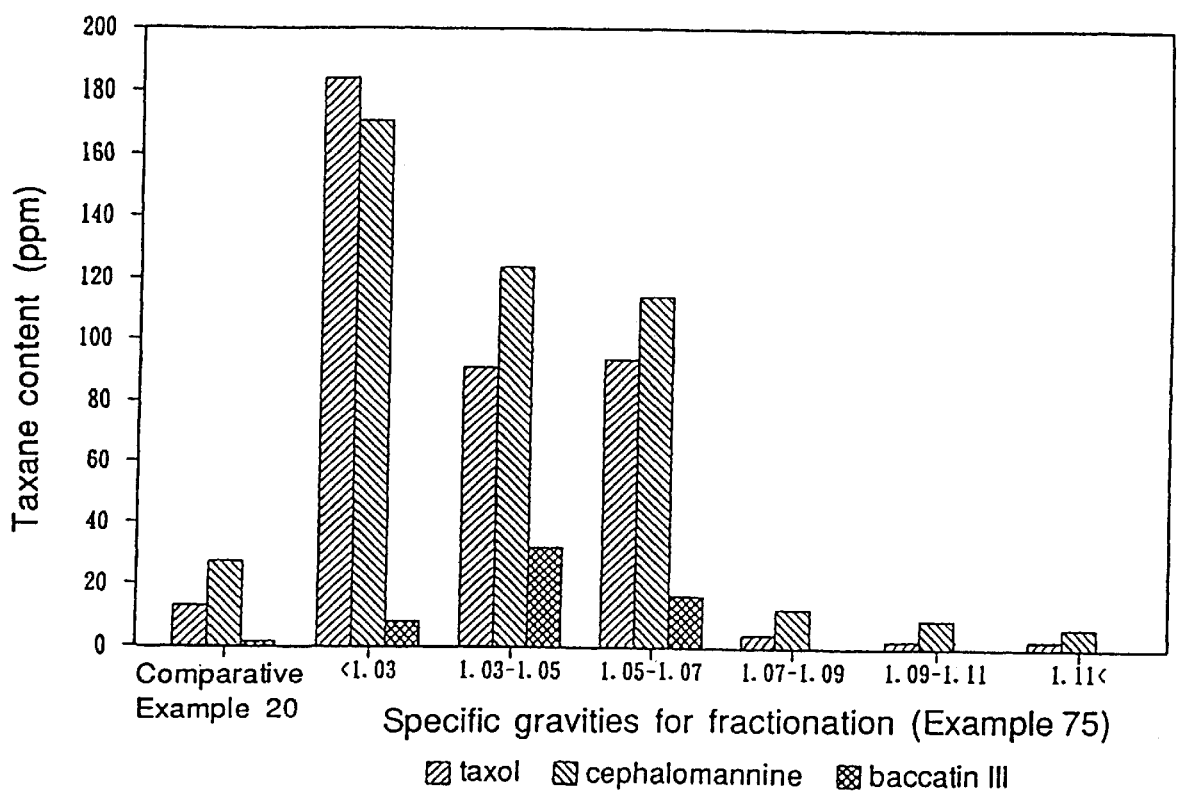
FIG. 5 is a graph showing the taxane content in the culture after the fractionation.

After completing the culture, cultured cells of *Taxus baccata* LINN were harvested by filtration and lyophilized, then the dry weight was measured to obtain the growth weight thereof per liter the liquid medium. Taxane-type diterpenes were extracted from the dried callus with methanol and the like, and they were determined by comparing with standard taxol, cephalomannine, and baccatin III using high performance liquid chromatography to measure the yields of the taxane-type diterpenes. The results are shown in Table 22, FIG. 4 and FIG. 5.

Comparative Example 20

The procedure of Example 75 was carried out except that fractionation according to the density gradient was not carried out after separation of the cell clusters by the stainless mesh. The results are shown in Table 22, FIG. 4 and FIG. 5.

Example 76

The procedure of Example 75 was carried out except that the cultured cells which have the same parent plant, but were induced to callus in different stage were used. Provided that the cells contained in a layer having the specific gravity of 1.07 or more were collected in one group and cultured. The results are shown in Table 22.

Comparative Example 21

The procedure of Example 76 was carried out except that fractionation according to the density gradient was not carried out after separation of the cell clusters by the stainless mesh. The results are shown in Table 22.

TABLE 22

|  | specific gravity range | cell yield (g/l) | content[*] of baccatin III (ppm) | content[*] of taxol (ppm) | content[*] of cephalo- mannine (ppm) |
|---|---|---|---|---|---|
| Comparative Example 20 | — | 12.6 | 1.5 | 13.0 | 27.5 |
| Example 75 | <1.03 | 12.5 | 7.9 | 184.0 | 170.3 |
|  | 1.03–1.05 | 12.5 | 32.1 | 90.8 | 123.7 |
|  | 1.05–1.07 | 12.2 | 16.3 | 93.5 | 114.1 |
|  | 1.07–1.09 | 12.6 | 0.0 | 3.9 | 12.3 |

TABLE 22-continued

|  | specific gravity range | cell yield (g/l) | content*) of baccatin III (ppm) | content*) of taxol (ppm) | content*) of cephalo-mannine (ppm) |
|---|---|---|---|---|---|
|  | 1.09–1.11 | 11.9 | 0.0 | 2.1 | 8.6 |
|  | 1.11< | 13.5 | 0.0 | 2.5 | 6.3 |
| Comparative Example 21 | — | 9.3 | 256.5 | 864.0 | 662.5 |
| Example 76 | 1.03–1.05 | 9.0 | 151.3 | 1660.5 | 1050.2 |
|  | 1.05–1.07 | 9.9 | 155.7 | 1140.8 | 804.0 |
|  | 1.07< | 9.5 | 19.0 | 333.1 | 161.3 |

*): The content was calculated by dividing the total amount of production (in the cell + in the medium) by the cell yield Reference Example 4

Figure 6:
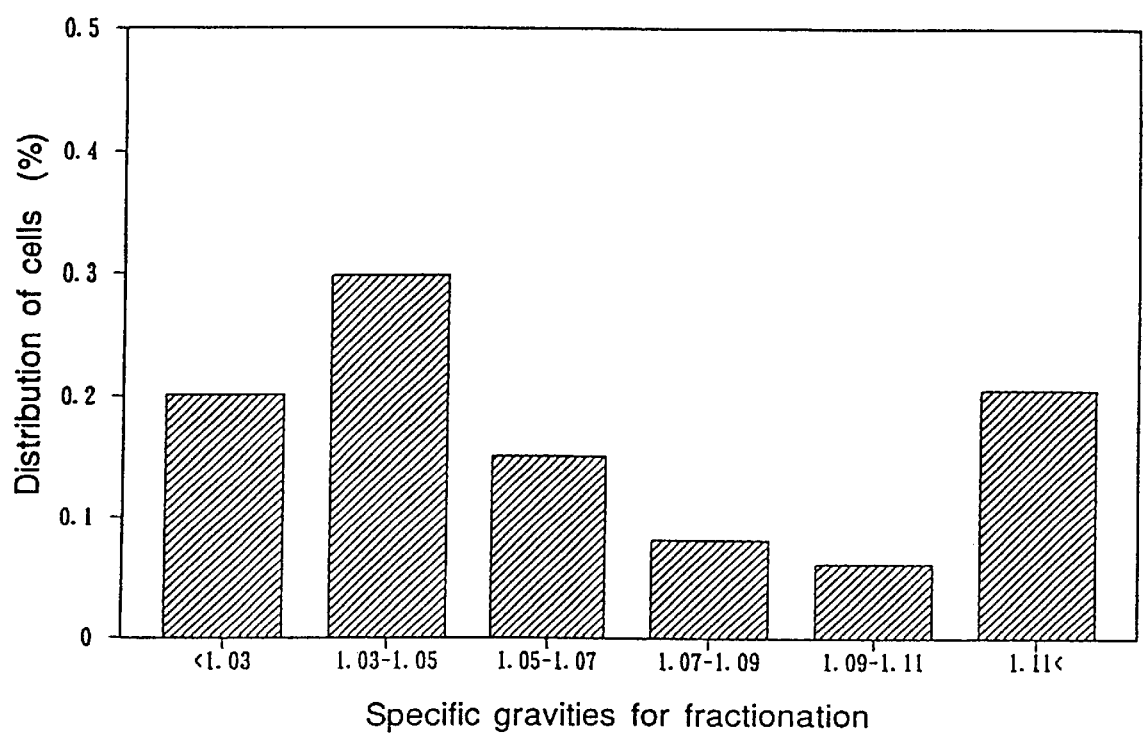
FIG. 6 is a graph showing the distribution of the cells at the fractionation.
Figure 7:
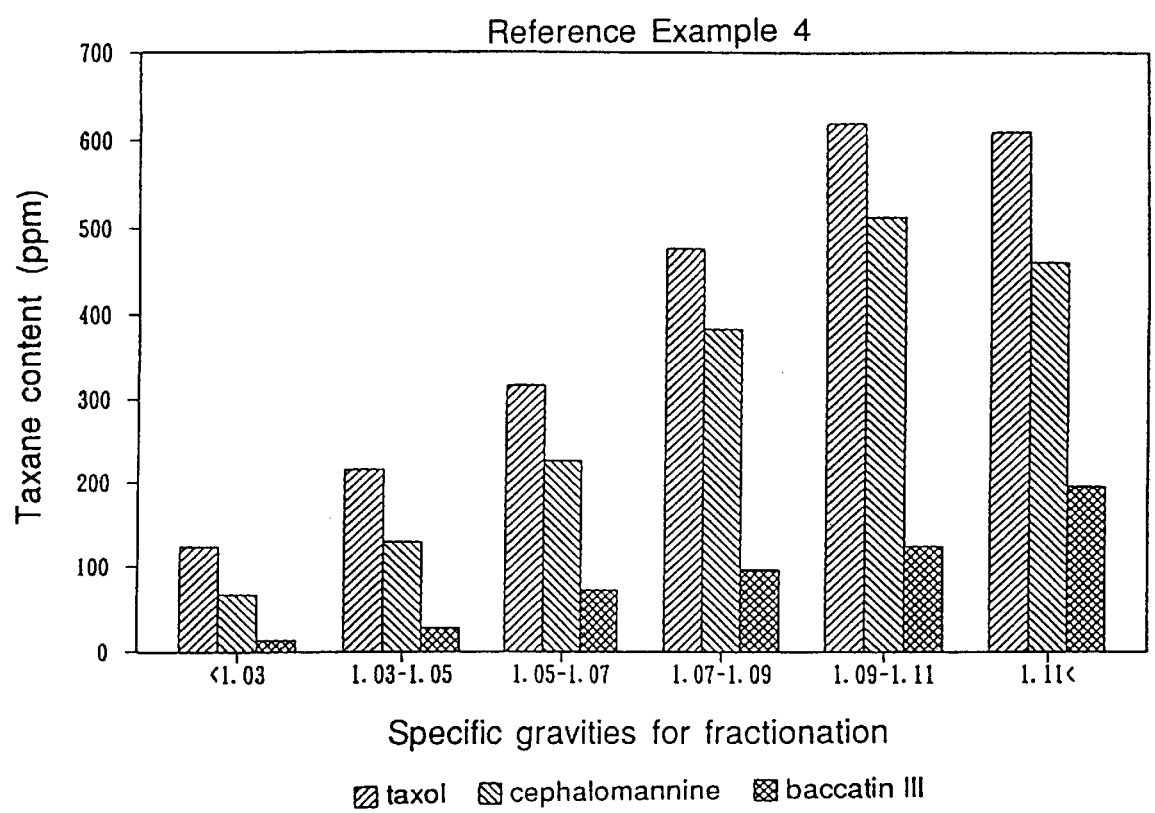
FIG. 7 is a graph showing the taxane content (in cell) at the fractionation.

About 0.2 g (fresh weight) of the cells obtained in Example 75 which were cultured after being fractionated into a layer having the specific gravity range of 1.03 or less (Table 22) were inoculated to a culture well having an inner diameter of 36 mm containing 3 ml of liquid Woody Plant Medium and shake culture was carried out at 25° C. for another 28 days. After completing the culture, the cells were again fractionated by the density gradient with specific gravities of 1.03, 1.05, 1.07, 1.09 and 1.11 (g/ml). Immediately after the density gradient fractionation, the cells were collected and the distribution of the fractionated cells and the contents of the taxane-type diterpenes were determined. The results are shown in Table 23, FIG. 6 and FIG. 7.

TABLE 23

|  | specific gravity range | distribution of cells (%) | content*) of baccatin III (ppm) | content*) of taxol (ppm) | content*) of cephalo-mannine (ppm) |
|---|---|---|---|---|---|
| Reference Example 4 | <1.03 | 20.2 | 13.9 | 123.9 | 66.5 |
|  | 1.03–1.05 | 29.8 | 28 1 | 216 1 | 128.7 |
|  | 1.05–1.07 | 15.1 | 71.7 | 315.5 | 226.0 |
|  | 1.07–1.09 | 8.1 | 96.2 | 475.8 | 382.6 |
|  | 1.09–1.11 | 6.2 | 123.5 | 619.4 | 511.8 |
|  | 1.11< | 20.5 | 195.2 | 609.6 | 460.2 |

*): The content was calculated by dividing the amount of production in the cell by the cell yield.

Example 77

One gram (fresh weight) of the same cultured cells that were used in Example 1 was inoculated to an Erlenmeyer flask containing 20 ml of a liquid containing $10^{-5}M$–$10^{-2}M$ of potassium peroxodisulfate and shaken at 25° C. for 21 days to carry out the first stage of the culture.

After completing the culture, the cultured cells were harvested by filtration and a part of the cells were used as seed cells for the second stage of the culture and the rest of the cells were subjected to the measurement of the cell yield and the taxane content in the cells. Accordingly, 1 g (fresh weight) of the cultured cells were inoculated to an Erlenmeyer flask containing 20 ml of liquid Woody Plant Medium to which naphthalenacetic acid had been added to give the concentration of $10^{-5}M$ and shake culture was carried out at 25° C. for 14 days. On the 14th day of the culture, methyl jasmonate was added to the medium to give the concentration in the medium of 100 μM and the culture was further continued for another 7 days. On the other hand, the rest of the cells obtained in the first stage of the culture were lyophilized, then the dry weight was measured to obtain the cell yield thereof per liter of the liquid medium. The content of taxol in the dried cells was measured by high performance liquid chromatography. The yield of the cells and the yield of taxol were measured for the cells obtained by second stage of the culture in the same manner as that for the cells obtained in the first stage of the culture. The results are shown in Table 24.

Comparative Example 22

The procedure of Example 77 was carried out except that potassium peroxodisulfate was not used. The results are shown in Table 24.

TABLE 24

|  | additives to be used in the first stage of the cultivation | | result of the first stage of the culture | | result of the second stage of the culture | |
|---|---|---|---|---|---|---|
|  | concentration of potassium peroxodisulfate in the medium | time for addition | yield of cells (g/l) | content of taxol (ppm) | yield of cells (g/l) | yield of taxol (ppm) |
| Example 77 | $10^{-5}M$ | 1st day | 17.1 | 97 | 15.6 | 14.0 |
| Example 77 | $10^{-4}M$ | 1st day | 16.2 | 250 | 15.0 | 20.4 |
| Example 77 | $5 \times 10^{-4}M$ | 1st day | 15.5 | 183 | 14.4 | 16.3 |
| Example 77 | $10^{-3}M$ | 1st day | 15.2 | 84 | 13.0 | 13.6 |
| Example 77 | $5 \times 10^{-3}M$ | 1st day | 14.0 | 45 | 12.1 | 11.7 |
| Comparative Example 22 | — | — | 16.5 | 53 | 15.4 | 10.1 |

Example 78

Figure 8:
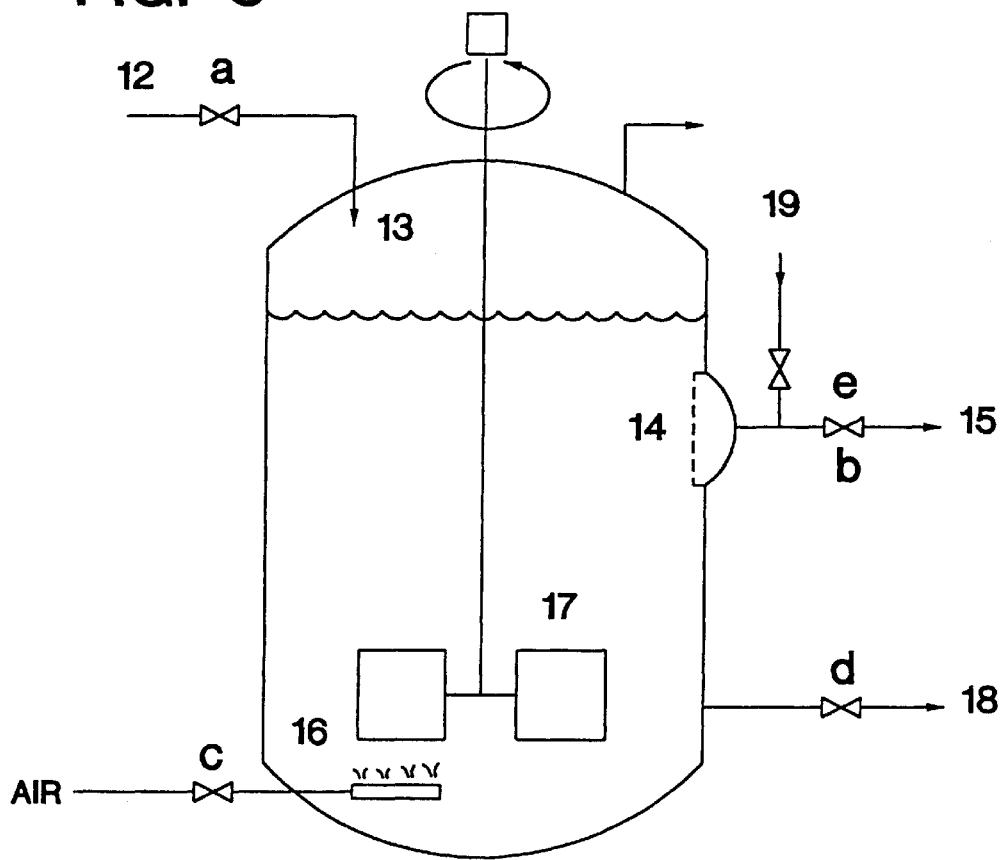
FIG. 8 is a diagram illustrating an example of a culture apparatus used for carrying out the tissue culture according to the sixth or the seventh invention of the present application. Each numeral and alphabet used in the FIG. 8 has the following meaning.

A hundred grams (fresh weight) of the same cultured cells that were used in Example 1 were inoculated in a tank for stirred tank culture (capacity of 2 liter; FIG. 8) filled with 1 liter of standard liquid Woody Plant Medium (sucrose concentration: 20 g/l, nitrate ion concentration: 14.7 mM, a-naphthalenacetic acid: $10^{-5}M$) to which 2 mM $[Ag(S_2O_3)_2]^{3-}$ had been added, and the culture was started at 25° C. in the dark at the agitation rate of 40 rpm, while air was fed at 0.1 liter per minute, and a medium containing 20 g/l of sucrose and 20 mM of sodium nitrate was supplied continuously in a period starting from the second day till the 14th day of the culture in such a manner that the amount of the sucrose added in one day became 2 g/l and the amount of nitrate ion added in one day became 2 mmol/l, and the culture solution was continuously taken out through a discharge opening, which was different from the nutrition source feed opening, and to which a stainless filter of 100 mesh was attached, at the same rate as that of the addition of the nutrition source solution (the medium renewing ratio in the culture vessel was 10% per day) to carry out stirred tank culture for 21 days. After completing the culture, the cultured cells and the medium were collected and the yield of taxol was measured in the same manner as that used in the said Example 1. The results are shown in Table 25.

Comparative Example 23

The procedure of Example 78 was carried out except that the nutrition source was not added midway. The results are shown in Table 25.

TABLE 25

| | yield of cells | yield of taxol (mg/l) | | |
|---|---|---|---|---|
| | (g dried weight/l) | from cells | from medium | total |
| Example 78 | 38 | 31 | 89 | 125 |
| Comparative Example 23 | 22 | 33 | 27 | 60 |

Example 79

Fifty grams (fresh weight) of the same cultured cells that were used in Example 1, and 1 liter of liquid Woody Plant Medium were transferred to a culture tank (capacity of 2 liter) and the culture was carried out at 25° C. in the dark at the agitation rate of 40 rpm, at the aeration speed of 0.1 liter per minute for 14 days. The precipitated cell volume (PCV) measured on the 14th day after starting the culture was 0.2 liter. From the 14th day, supply of a fresh medium, wherein 3 mM $[Ag(S_2O_3)_2]^{3-}$ had been added to the medium of the same composition as that of the initial medium, as well as taking out of a culture solution which was free from cells were started. The amount of the fresh medium to be supplied per day was ⅔ of the PCV at that time and the amount of the culture solution free from the cells to be taken out was controlled to be 1 liter. On the 35th day after starting the culture, PCV reached 0.6 liter. After that, the stationary state was maintained by taking out the culture solution containing cells once a day to keep the average PCV to 0.6 liter and by taking out the culture solution free from cells to keep the amount of the culture solution to 1 liter. The culture was carried out for 90 days after the start of the culture. The amount of the fresh medium supplied during the stationary state of 60 days was 15 liters, the amount of the medium taken out of the culture tank was 14 liters and the amount of the cells obtained was 0.15 kg (dry weight) and the specific growth rate $\mu$ was 0.08 $(day^{-1})$, the average medium renewing ratio was 2.88. The results of the analysis of cells and medium taken out from the culture tank under stationary state showed that 525 mg of taxol was produced. That was equal to the productivity of 8.8 mg/liter/day.

The amount of the taxol contained in the cells and the medium were measured in the same manner as that used in Example 1.

Example 80

Fifty grams (fresh weight) of the same cultured cells that were used in Example 1 and 1 liter of liquid Woody Plant Medium were transferred to a culture tank (capacity of 2 liters) and the culture was carried out in the dark, at the agitation rate of 40 rpm, at 25° C. for 14 days, while an air to which 2% carbon dioxide gas had been added was fed at 0.1 liter per minute. After completing the culture, the cells and the medium were collected and 15.2 g of dry cells were obtained. Determination of the amount of taxol contained in the cells and in the medium which was carried out in the same manner as that used in Example 1 showed that 31 mg of taxol was produced.

Comparative Example 24

The procedure of Example 1 was carried out except that jasmone was added instead of methyl tuberonate to give the final concentration of 0.1–1000 μM. The results are shown in Table 26.

Comparative Example 25

The procedure of Comparative Example 24 was carried out except that jasmone was not added. The results are shown in Table 26.

TABLE 26

| | concentration of jasmone (μM) | cell yield (g/l) | yield*) of baccatin III (mg/l) | yield*) of taxol (mg/l) | yield*) of cephalomannine (mg/l) |
|---|---|---|---|---|---|
| Comparative Example 24 | 0.1 | 12.2 | 0.3 | 3.0 | 1.2 |
| Comparative Example 24 | 1 | 12.1 | 0.4 | 3.2 | 1.0 |
| Comparative Example 24 | 10 | 11.3 | 0.3 | 3.3 | 0.8 |
| Comparative Example 24 | 100 | 11.3 | 0.3 | 3.2 | 0.6 |
| Comparative Example 24 | 1000 | 10.9 | 0.2 | 2.5 | 0.8 |
| Comparative Example 25 | 0 | 12.2 | 0.2 | 2.8 | 1.5 |

*): The yield was calculated based on the total amount of production (in the cell + in the medium)

Industrial Applicability

The present invention allows industrial production of a taxane-type diterpene including taxol which is useful as a therapeutic agent for ovarian cancer, mammary cancer, lung cancer and the like.

What is claimed is:

1. A method of producing a taxane ring-containing alkaloid compound, which comprises:

culturing a tissue or a cell of a plant belonging to the genus Taxus which produces a taxane ring-containing alkaloid compound, in a nutrient medium and in the presence of at least one complex ion containing a heavy metal in a concentration of $10^{-4}$M to $10^{-3}$M, and recovering the taxane ring-containing alkaloid compound from the resulting cultures.

2. The method according to claim 1, wherein the heavy metal is silver.

3. The method according to claim 2, wherein the complex ion containing silver is at least one ion selected from the group consisting of $(Ag(S_2O_3)_2)^{3-}$ and $(Ag(S_2O_3)_3)^{5-}$.

4. The method according to claim 2, wherein the complex ion containing silver is at least one ion selected from the group consisting of $(Ag(NH_3)_2)^+$, $(Ag(CN)_2)^-$, $(Ag(CN)_3)^{2-}$, $Ag(SCN)_2)^-$, and $Ag(SCN)_4)^{3-}$.

5. The method according to claim 1, wherein the heavy metal is cobalt.

6. The method according to claim 5, wherein the complex ion containing cobalt is at least one ion selected from the group consisting of pentaammineaquacobalt ion, nitropentaamminecobalt ion, dichlorotetraamminecobalt ion, dinitrotetraanxminecobalt ion, carbonatotetraamminecobalt ion, tetranitrodiamminecobalt ion, hexanitrocobalt ion, tris(ethylenediamine)cobalt ion, dichlorobis(ethylenediamine)cobalt ion, tris(oxalato)cobalt ion, hexacyanocobalt ion, and (ethylenediaminetetraacetato)cobalt ion.

7. The method according to claim 1, wherein the taxane ring-containing alkaloid compound is at least one compound selected from the group consisting of taxol, 7-epitaxol, baccatin III, 7-epibaccatin III, cephalomannine, 7-epicephalomannine, 10-deacetylbaccatin III, 10-deacetylcephalomannine, 10-deacetyltaxol, taxagifine, xylosyl cephalomannine, and xylosyl taxol.

8. The method according to claim 1, wherein the plant belonging to genus Taxus is at least one plant selected from the group consisting of *Taxus baccata* LINN, *Taxus cuspidata* SIEB. et ZUCC, *Taxus cuspidata* SIEB. et ZUCC var. nana REHDER, *Taxus brevifolia* NUTT, *Taxus canadiensis* MARSH, *Taxus chinensis*, and *Taxus media*.

9. The method according to claim 1, wherein after culturing, cells of the plant which produces the taxane ring-containing alkaloid compound are fractionated into a plurality of layers according to the difference in their specific gravities, and cells contained in at least one layer are cultured.

10. The method according to claim 1, wherein the tissues or the cells of the plant which produce the taxane ring-containing alkaloid compound are cultured by controlling the oxygen concentration in a gas phase in a culture vessel to less than the oxygen concentration in the atmosphere, from the initial stage of the culture, or by controlling the dissolved oxygen concentration in a fluid medium which is in contact with the tissues or the cells to less than the saturated dissolved oxygen concentration at that temperature, from the initial stage of the culture.

11. A method of producing a taxane ring-containing alkaloid compound wherein tissues or cells of a plant which produce a taxane ring-containing alkaloid compound are cultured by carrying out a two-stage culture, comprising a first stage using a medium to which an oxidizing agent or a water soluble organic compound containing oxygen is added and a second stage which is carried out according to the production method of claim 1, then the taxane ring-containing alkaloid compound is recovered from the resulting cultures.

12. The method according to claim 1, wherein the tissues or the cells of the plant which produce the taxane ring-containing alkaloid compound are cultured by inoculating the tissues or the cells in a culture medium containing a saccharide in a concentration of 2–50 g/l, and/or nitrate ion in a concentration of 2–50 mmol/1, then by adding a nutrient source solution containing the saccharide in an amount of 0.2–5 g/l, and/or nitrate ion in an amount of 0.2–5 mmol/1 per day based on the initial volume of the said culture medium, continuously or intermittently to the culture medium, then the taxane ring-containing alkaloid compound is recovered from the resulting cultures.

13. The method according to claim 12, wherein the culture is carried out while the culture medium is renewed by adding the nutrient source solution and separating and removing the same volume of the culture medium from the tissues or the cells, and the taxane ring-containing alkaloid compound is recovered from at least one substance selected from the resulting tissues and/or cells, the culture medium recovered during the culture and obtained at the end of the culture.

14. The method according to claim 1, wherein a fresh medium is added continuously or intermittently in such a way that the specific renewing ratio defined by the dimensionless number $F=V_f/V V_\mu$ (wherein, V is the total volume of the culture solution in a culture tank, $V_f$ is the feed speed of the fresh medium, and $\mu$ is the specific growth rate of the tissues or the cells) is in the range of 0.1 to 10, and the taxane ring-containing alkaloid compound is recovered from the culture medium and the tissues or the cells contained in the culture medium which is continuously or intermittently taken out from the tank and/or from the culture medium containing no tissue and cell which is continuously or intermittently taken out from the tank.

15. The method according to claim 1, wherein the tissues or the cells of the plant which produce the taxane ring-containing alkaloid compound are cultured in contact with a gas phase containing oxygen and 0.03–10% of carbon dioxide.

* * * * *

UNITED STATES PATENT AND TRADEMARK OFFICE
CERTIFICATE OF CORRECTION

PATENT NO.    : 6,403,343 B2                                                Page 1 of 1
DATED         : June 11, 2002
INVENTOR(S)   : Yukihito Yukimune et al.

It is certified that error appears in the above-identified patent and that said Letters Patent is hereby corrected as shown below:

Title page,
Item [54], please correct the title from "METHOD OF PRODUCING A TAXANE-TYPE DITERPENE AND A METHOD OF OBTAINING CULTURED CELLS WHICH PRODUCE THE TAXANE-TYPE DILTERPENE AT A HIGH RATE" to -- METHOD OF PRODUCING A TAXANE-TYPE DITERPENE AND A METHOD OF OBTAINING CULTURED CELLS WHICH PRODUCE THE TAXANE-TYPE DITERPENE AT A HIGH RATE --.

Signed and Sealed this

Fourth Day of March, 2003

JAMES E. ROGAN
*Director of the United States Patent and Trademark Office*